(12) United States Patent
Cho et al.

(10) Patent No.: US 12,098,209 B2
(45) Date of Patent: Sep. 24, 2024

(54) FUSION PROTEIN COMPRISING IDS AND USE THEREOF

(71) Applicant: MOGAM INSTITUTE FOR BIOMEDICAL RESEARCH, Yongin-si (KR)

(72) Inventors: Ki Joon Cho, Yongin-si (KR); Mijung Lee, Yongin-si (KR); Eun Jung Song, Yongin-si (KR); Ki Su Kim, Yongin-si (KR); Kwan Yub Kang, Yongin-si (KR); Eui Cheol Cho, Yongin-si (KR)

(73) Assignee: MOGAM INSTITUTE FOR BIOMEDICAL RESEARCH, Yongin-si (KR)

( * ) Notice: Subject to any disclaimer, the term of this patent is extended or adjusted under 35 U.S.C. 154(b) by 732 days.

(21) Appl. No.: 17/285,367

(22) PCT Filed: Oct. 18, 2019

(86) PCT No.: PCT/KR2019/013730
§ 371 (c)(1),
(2) Date: Apr. 14, 2021

(87) PCT Pub. No.: WO2020/085721
PCT Pub. Date: Apr. 30, 2020

(65) Prior Publication Data
US 2021/0324094 A1    Oct. 21, 2021

(30) Foreign Application Priority Data
Oct. 26, 2018    (KR) .................. 10-2018-0129201

(51) Int. Cl.
*C07K 16/28*    (2006.01)
*A61K 38/46*    (2006.01)
(Continued)

(52) U.S. Cl.
CPC ........ *C07K 16/2869* (2013.01); *A61K 38/465* (2013.01); *C12N 9/16* (2013.01);
(Continued)

(58) Field of Classification Search
CPC ............ C07K 16/2869; C07K 2317/33; C07K 2317/526; C07K 2317/55;
(Continued)

(56) References Cited

U.S. PATENT DOCUMENTS 9,611,323 B2 * 4/2017 Dennis .................. C07K 16/18
2015/0284475 A1 10/2015 Zhou et al.

FOREIGN PATENT DOCUMENTS

JP         2013-507131 A      3/2013
KR    10-2015-0039798 A      4/2015
(Continued)

OTHER PUBLICATIONS

Pardridge WM, Kang YS, Buciak JL, Yang J. Human insulin receptor monoclonal antibody undergoes high affinity binding to human brain capillaries in vitro and rapid transcytosis through the blood-brain barrier in vivo in the primate. Pharm Res. Jun. 1995;12(6):807-16. doi: 10.1023/a:1016244500596. (Year: 1995).*
(Continued)

*Primary Examiner* — Jeffrey Stucker
*Assistant Examiner* — Laura Ann Essex
(74) *Attorney, Agent, or Firm* — Sughrue Mion, PLLC

(57) ABSTRACT

An asymmetric fusion protein in which a fragment of an antibody binding to an insulin receptor, an iduronate-2-sulfatase (IDS) enzyme, and an Fc region are fused, and a use thereof are disclosed. The fusion protein can cross the blood-brain barrier (BBB) to deliver the IDS enzyme to the brain. Therefore, a pharmaceutical composition containing the fusion protein as an active ingredient can be used as a therapeutic agent for a central nervous system disease and
(Continued)

particularly, is expected to prevent and treat various diseases caused by ribosome accumulation.

16 Claims, 12 Drawing Sheets

Specification includes a Sequence Listing.

(51) Int. Cl.
*A61K 39/00* (2006.01)
*C12N 9/16* (2006.01)

(52) U.S. Cl.
CPC .............. *C12Y 301/06013* (2013.01); *A61K 2039/505* (2013.01); *C07K 2317/33* (2013.01); *C07K 2317/526* (2013.01); *C07K 2317/55* (2013.01); *C07K 2317/565* (2013.01); *C07K 2317/622* (2013.01); *C07K 2317/76* (2013.01); *C07K 2317/92* (2013.01); *C07K 2319/30* (2013.01)

(58) Field of Classification Search
CPC ........ C07K 2317/565; C07K 2317/622; C07K 2317/76; C07K 2317/92; C07K 2319/30; A61K 38/465; A61K 2039/505; C12N 9/16; C12Y 301/06013
See application file for complete search history.

(56) References Cited

FOREIGN PATENT DOCUMENTS

| KR | 10-2016-0011198 A | 1/2016 | |
|---|---|---|---|
| WO | WO-2011044542 A1 * | 4/2011 | ............. A61P 25/28 |
| WO | 2014/033074 A1 | 3/2014 | |
| WO | 2014/079000 A1 | 5/2014 | |
| WO | 2014/189973 A2 | 11/2014 | |
| WO | WO-2018158719 A1 * | 9/2018 | ........... C07K 16/244 |

OTHER PUBLICATIONS

Kishnani, P.S. (2015). Challenges of Enzyme Replacement Therapy. In: Rosenberg, A., Demeule, B. (eds) Biobetters. AAPS Advances in the Pharmaceutical Sciences Series, vol. 19. Springer, New York, NY. https://doi.org/10.1007/978-1-4939-2543-8_2 (Year: 2015).*

International Searching Authority, Written opinion in Korean for PCT/KR2019/013730 dated Jan. 23, 2020.

International Searching Authority, International search report for PCT/KR2019/013730 dated Jan. 23, 2020.

Lu et al., "Expression in CHO Cells and Pharmacokinetics and Brain Uptake in the Rhesus Monkey of an IgG-Iduronate-2-Sulfatase Fusion Protein", Biotechnology and Bioengineering, vol. 108, No. 8, Aug. 2011, pp. 1954-1964.

* cited by examiner

| LCDR3 | HCDR3 |
|---|---|
| WT: LEYNNLPLT (SEQ ID NO: 23) | WT: HPSYGTVNHAYFDV (SEQ ID NO: 24) |

Increase of Affinity

| LCDR3 | HCDR3 |
|---|---|
| HL009: LEYPNLPLT (SEQ ID NO: 25) | H031: HPRYGTVNHAYFDV (SEQ ID NO: 26) |
| | HL009: HPRYGTVNHAYFDV (SEQ ID NO: 26) |

Decrease of Affinity

| LCDR3 | HCDR3 |
|---|---|
| L016: LEYNVLPLT (SEQ ID NO: 27) | H118: HPTYGTVNHAYFDV (SEQ ID NO: 29) |
| L113: LEYNSLPLT (SEQ ID NO: 28) | |

[FIG. 5]
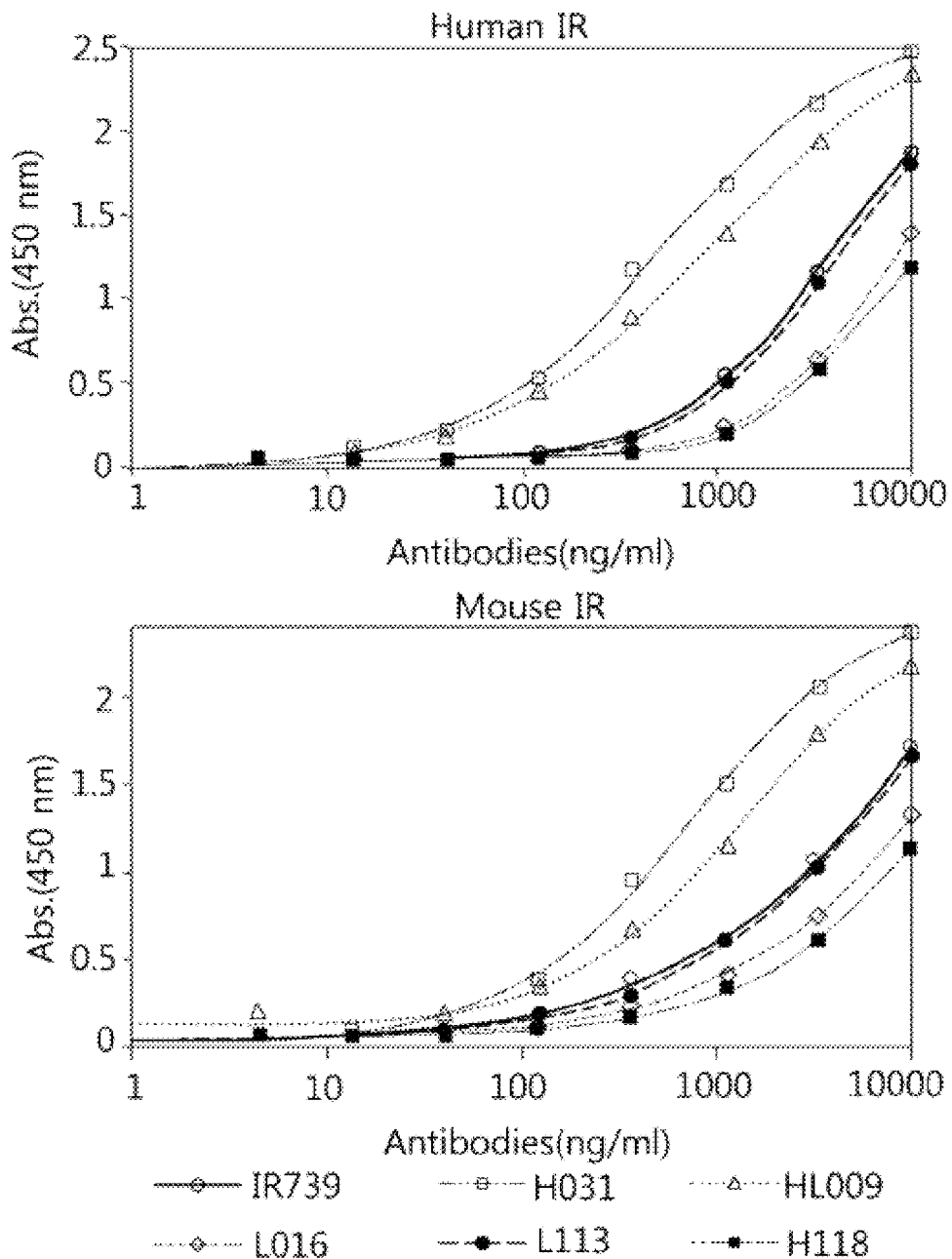

[FIG. 6]
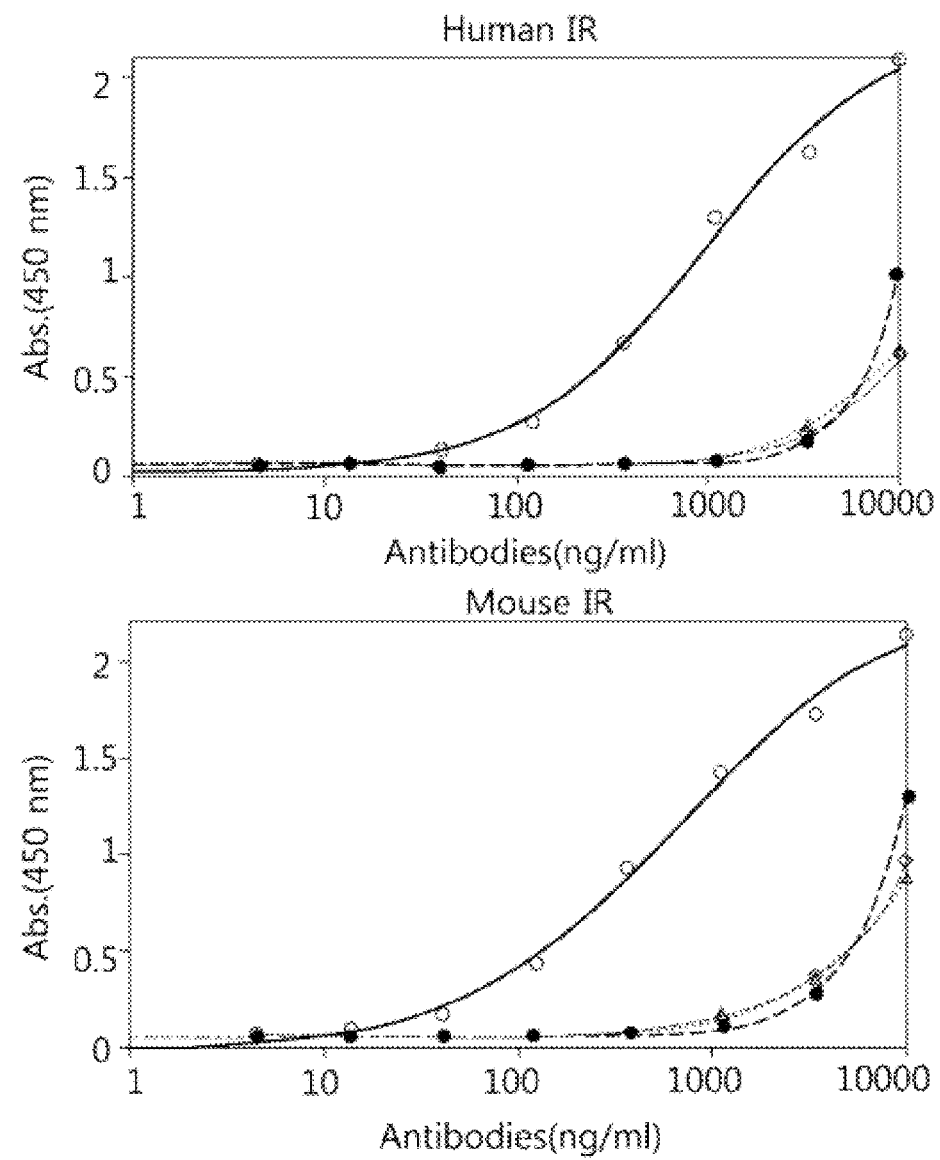

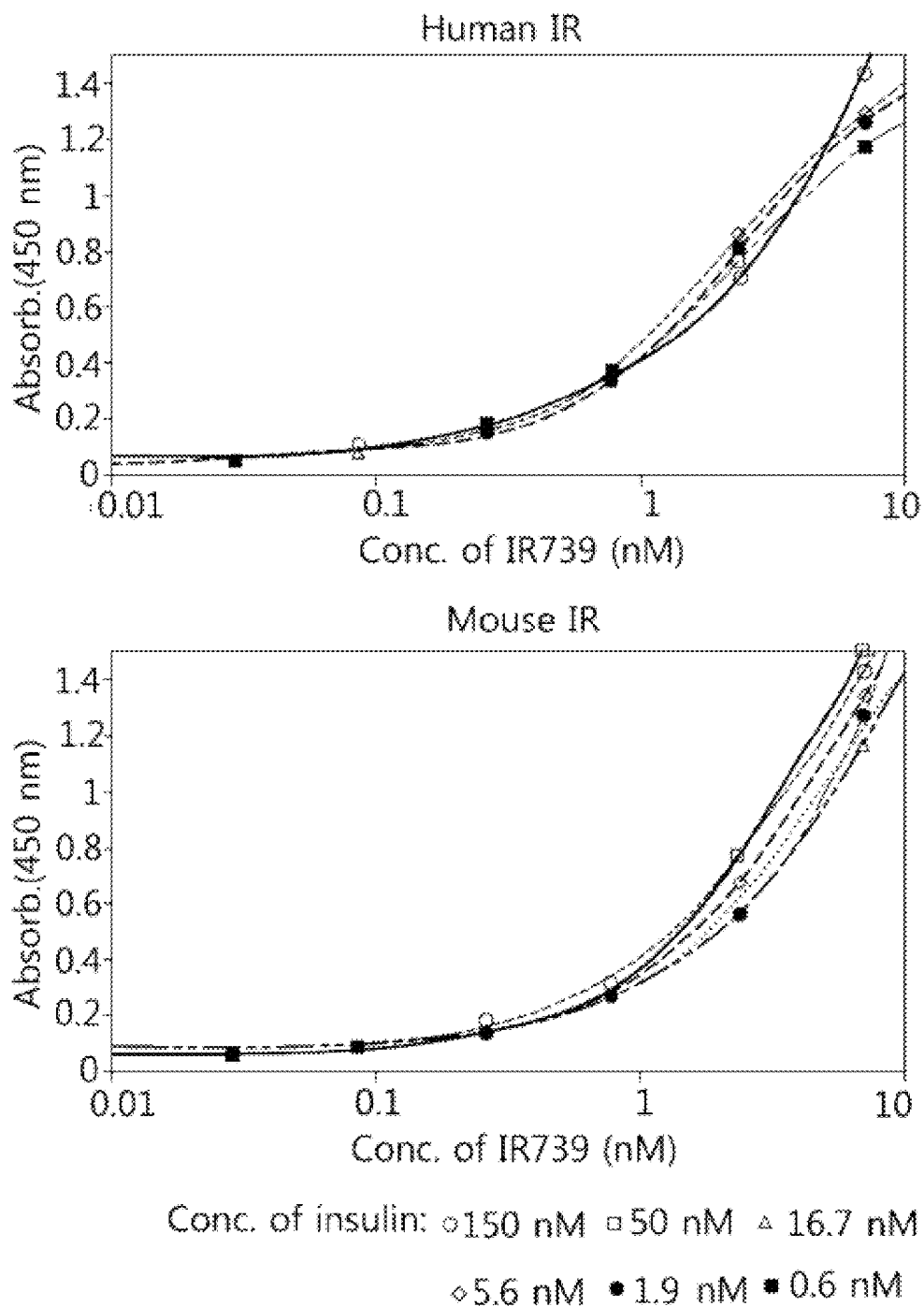
[FIG. 7]

[FIG. 8]
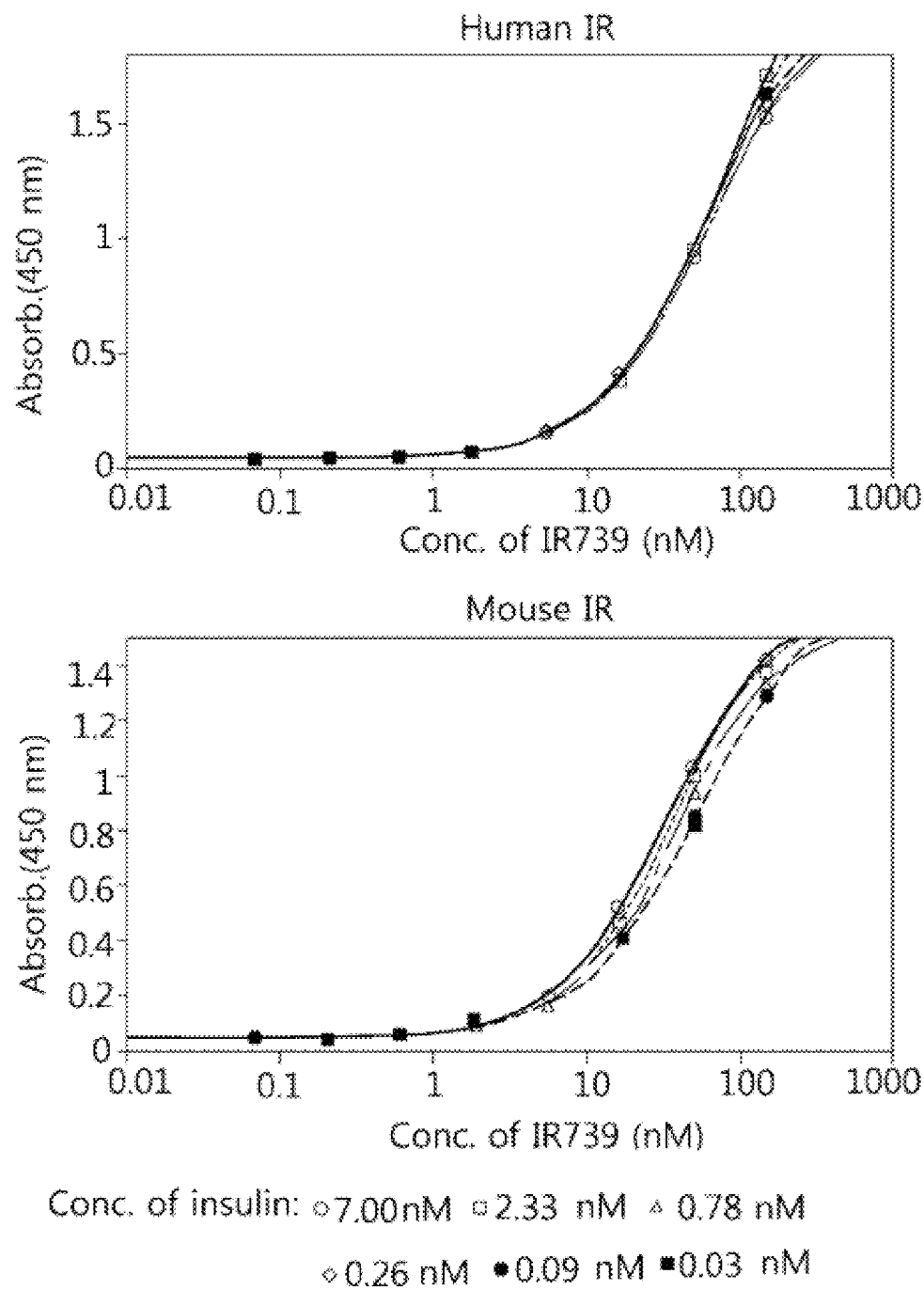

[FIG. 9]
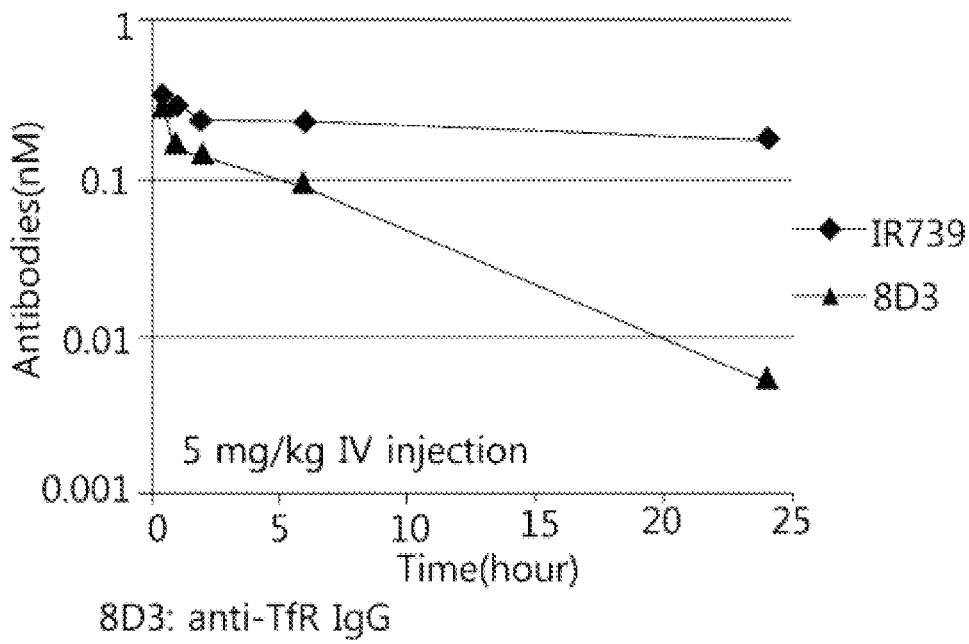
8D3: anti-TfR IgG
[FIG. 10]
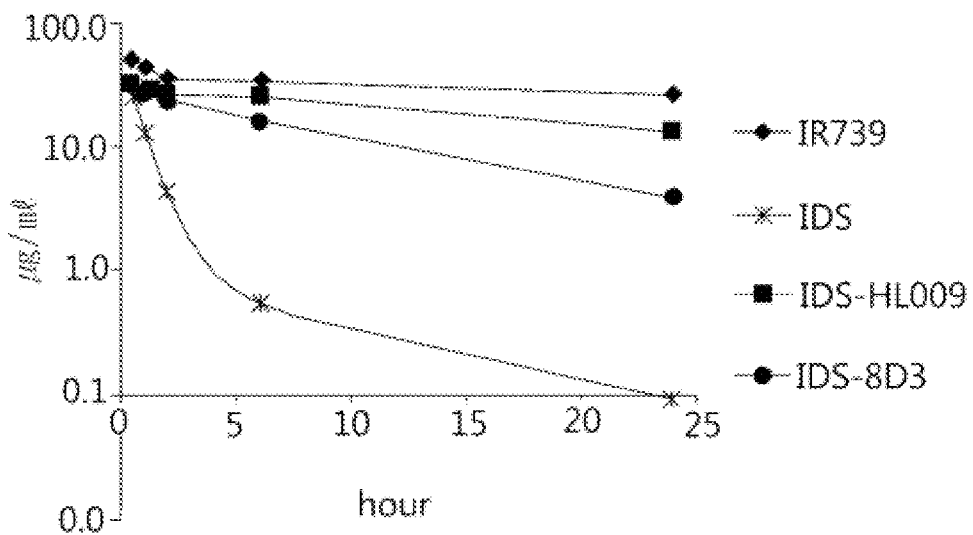

FUSION PROTEIN COMPRISING IDS AND USE THEREOF

CROSS-REFERENCE TO RELATED APPLICATIONS

This application is a National Stage of International Application No. PCT/KR2019/013730 filed Oct. 18, 2019, which claims priority under U.S.C. § 119(a) to Korea Patent Application No. 10-2018-0129201 filed on Oct. 26, 2018.

INCORPORATION BY REFERENCE OF SEQUENCE LISTING

The content of the electronically submitted sequence listing, file name: Q262621_Substitute_Sequence_Listing_as_filed.txt; size: 36.1 KB; and date of creation: Mar. 2, 2024, filed herewith, is incorporated herein by reference in its entirety.

TECHNICAL FIELD

The present invention relates to a fusion protein comprising iduronate-2-sulfatase (IDS) and a use thereof, and more specifically, to a fusion protein, in which the IDS enzyme and a fragment of an antibody binding to an insulin receptor are fused, and a use thereof.

BACKGROUND ART

Hunter syndrome (mucopolysaccharidosis II) is one of the diseases that occur in the central nervous system (CNS), and is caused by mutations in iduronate-2-sulfatase (IDS). IDS is an enzyme essential for decomposition of glycosaminoglycan (GAG). In a case where activity of IDS is decreased or lost, GAG accumulates in tissues and cells, which causes a disease. Currently, Hunterase and Elaprase are used as therapeutic agents for Hunter syndrome. However, these therapeutic agents for central nervous system diseases are problematic in that delivery of the therapeutic agents to the brain is not achieved properly because they do not pass through the blood-brain-barrier (BBB) after being injected into the patient's vein.

Meanwhile, cerebrovascular cells limit, through the BBB, transfer of substances between the blood and the brain, and thus protect the brain. Therefore, it is difficult to apply substances such as antibodies or enzymes, which circulate through blood vessels in the body, as therapeutic agents for diseases occurring in the central nervous system (CNS), because such substances generally do not pass through the BBB and thus their transfer to the brain is restricted.

It has been subsequently found that transferrin or insulin can be delivered to the brain, through proteins expressed on the surface of cerebrovascular cells, such as transferrin receptor (TfR) or insulin receptor (IR), using a receptor-mediated transcytosis (RMT) mechanism. This mechanism has been used to develop a method of delivering a therapeutic agent to the brain. Recently, techniques have been developed which can deliver various substances, such as IDS therapeutic agents, to the brain using anti-TfR antibodies that can pass through the BBB (Korean Patent Publication Nos. 10-2016-0011198 and 10-2015-0039798).

Therefore, there is a need to develop an IDS therapeutic agent that has high affinity for a BBB receptor and has excellent BBB passage efficiency.

DISCLOSURE OF INVENTION

Technical Problem

Accordingly, the present inventors have developed an IDS enzyme therapeutic agent capable of passing through the BBB. Specifically, an object of the present invention is to provide an asymmetric fusion protein in which a fragment of an antibody binding to an insulin receptor, an IDS enzyme, and an Fc region are fused, and a use thereof.

Solution to Problem

In order to achieve the above-mentioned object, the present invention provides a fusion protein, comprising a first domain that includes a fragment of an antibody binding to an insulin receptor, a second domain that includes a protein having iduronate-2-sulfatase (IDS) activity, and an Fc region; and a method for preparing the same.

In addition, the present invention provides a pharmaceutical composition for preventing or treating a central nervous system disease, comprising the fusion protein as an active ingredient.

In addition, the present invention provides a method for preparing a fusion protein, comprising steps of: causing a fragment of an antibody binding to an insulin receptor to be bound to an Fc region, to prepare a first monomer; causing iduronate-2-sulfatase (IDS) to be bound to a heterodimeric Fc region, to prepare a second monomer; and mixing the first monomer with the second monomer.

In addition, the present invention provides a use of the fusion protein for preventing or treating a central nervous system disease.

In addition, the present invention provides a use of the fusion protein for manufacture of a medicament for preventing or treating a central nervous system disease.

In addition, the present invention provides a method for preventing or treating a central nervous system disease, comprising a step of administering, to an individual, the fusion protein or the pharmaceutical composition comprising the fusion protein.

Advantageous Effects of Invention

The fusion protein according to the present invention can effectively pass through the BBB so that an IDS enzyme therapeutic agent is delivered to the brain. Therefore, a pharmaceutical composition comprising the fusion protein as an active ingredient can be used as a therapeutic agent for a central nervous system disease. In particular, the pharmaceutical composition is expected to be able to prevent or treat various diseases caused by accumulation of lysosomes. In addition, from the viewpoint that the fusion protein exhibits excellent cross-reactivity with an animal BBB receptor and a human BBB receptor, the fusion protein has an advantage that the fusion protein, which has been applied to various disease animal models, can be directly applied to clinical studies.

BRIEF DESCRIPTION OF DRAWINGS

FIG. 3 illustrates CDR3 sequences of antibody variants (H031, HL009, L016, L113, and H118) binding to an insulin receptor.

FIG. 5 illustrates results obtained by comparing binding affinity of IR739 and variants of IR739 (H031, HL009, L016, L113, and H118) to a human insulin receptor and a mouse insulin receptor.

FIG. 6 illustrates results obtained by comparing binding affinity of IR739 and fusion proteins (IDS-IR739, IDS-HL009, and IDS-H031) to a human insulin receptor and a mouse insulin receptor.

FIG. 7 illustrates results obtained by comparing an interaction effect between insulin and IR739 on an insulin receptor, depending on changes in IR739 concentration.

FIG. 8 illustrates results obtained by comparing an interaction effect between insulin and IR739 on an insulin receptor, depending on changes in insulin concentration.

FIG. 9 illustrates a half-life of IR739 in mouse blood.

FIG. 10 illustrates half-lives of IDS and IDS-HL009 in mouse blood.

BEST MODE FOR CARRYING OUT THE INVENTION

Figure 1:
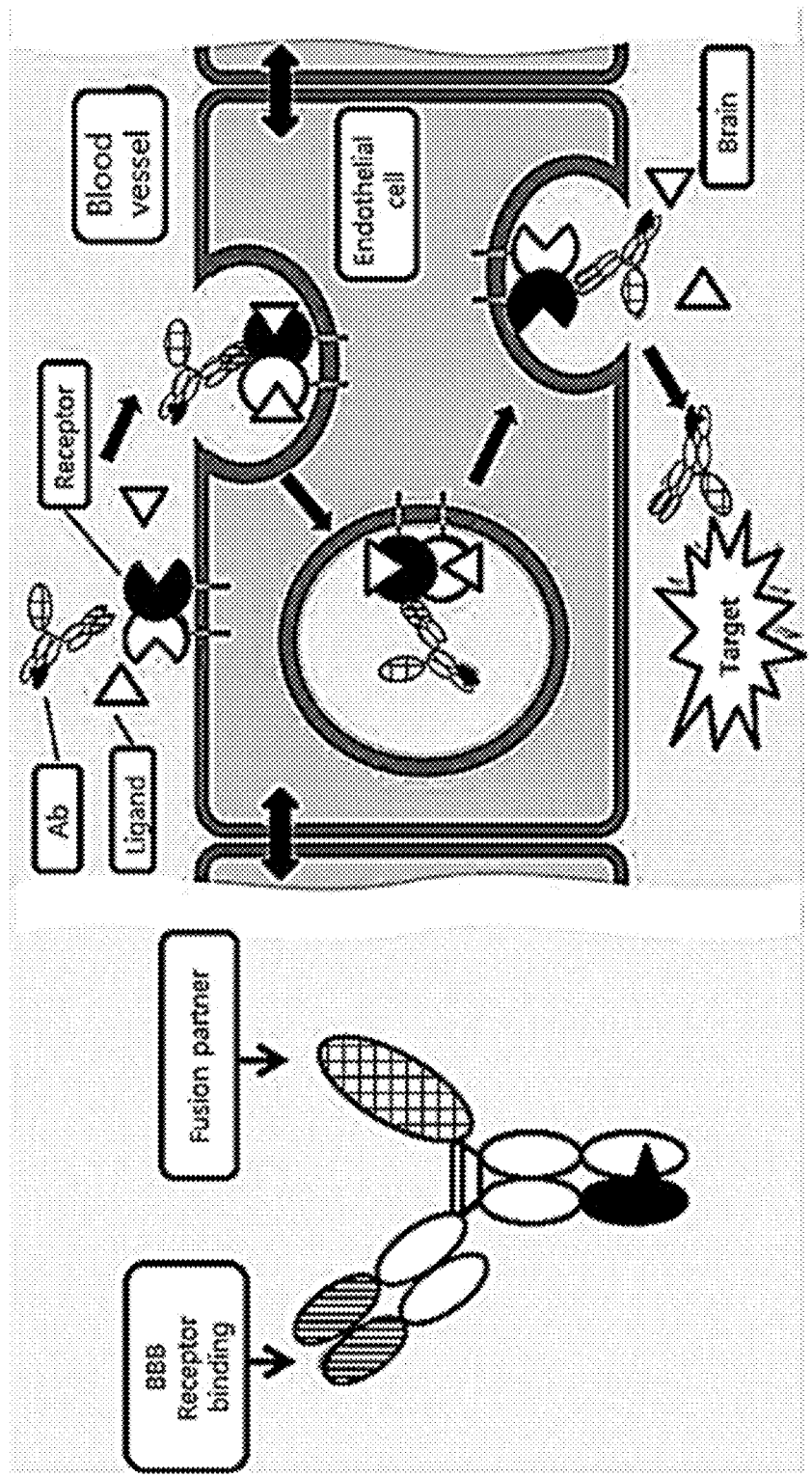
FIG. 1 illustrates schematic diagrams for the structure and the mechanism of action of the fusion protein.

In an aspect of the present invention, there is provided a fusion protein, comprising a first domain that includes a fragment of an antibody binding to an insulin receptor, and a second domain that includes a protein having iduronate-2-sulfatase (IDS) activity.

The term "insulin receptor", as used herein, refers to a transmembrane receptor protein that is expressed on cells and is capable of transporting insulin. Here, the insulin receptor can act as one of blood-brain barrier (BBB) receptors. The blood-brain barrier receptors include insulin receptor, insulin-like growth factor receptor (IGF-R), transferrin receptor, low density lipoprotein (LDL) receptor, glucose transporter 1 (Glut1), heparin-binding epidermal growth factor-like growth factor (HB-EGF), and the like; and these are extracellular transmembrane receptor proteins that are capable of transporting molecules across the BBB or that can be used to transport administered exogenous molecules.

In an embodiment of the present invention, the fusion protein can bind to the extracellular domain (ECD) of a human insulin receptor and pass through the BBB, so that the fused IDS can be delivered to the brain.

The term "antibody", as used herein, refers to an immunoglobulin (Ig) molecule that is immunologically reactive with a certain antigen, the molecule being a protein molecule that plays a role as a receptor specifically recognizing the antigen. The antibody means a concept encompassing both whole antibodies and fragments thereof (antibody fragments).

The term "iduronate-2-sulfatase (IDS)", as used herein, refers to an enzyme essential for decomposition of lysosomal glycosaminoglycan (GAG). In a case where a mutation occurs in IDS or a case where IDS has decreased activity or becomes inactive, GAG accumulates in most tissues and cells, which may cause a disease. Here, the IDS may have the amino acid sequence of SEQ ID NO: 21.

In an embodiment of the present invention, the fusion protein may further comprise an Fc region, and the Fc region may be derived from the heavy chain constant region (CH) of IgG1, IgG2, IgG3, or IgG4. In addition, the Fc region may be heterodimeric; and one of the heterodimeric Fc may have a knob structure, and the other may have a hole structure. The knob or hole structure may be located at CH3 in the Fc region.

The term "Fc region", as used herein, refers to a C-terminal region of an immunoglobulin heavy chain that contains a portion of a constant region. The Fc region usually includes CH2 and CH3 of an antibody heavy chain constant region. In addition, the Fc region includes a wild-type Fc region and a variant Fc region.

In an embodiment of the present invention, the first domain may be a Fab or scFv region of an antibody binding to an insulin receptor. The term "Fab", as used herein, refers to one that includes variable and constant regions of a light chain, and variable and CH1 regions of a heavy chain. The term "scFv", as used herein, refers to one that includes a heavy chain variable region and a light chain variable region of an antibody, and may be composed of "light chain variable region (VL)-linker-heavy chain variable region (VH)." The linker refers to an amino acid sequence having a certain length which functions to artificially link the heavy chain variable region to the light chain variable region.

The first domain includes CDRs, and these CDRs confer binding specificity for a certain antigen, in which a set of the CDRs (CDR1, CDR2, CDR3) may provide a binding site for the antigen.

In an embodiment of the present invention, the first domain may include a heavy chain variable region (VH) that includes H-CDR1 having the amino acid sequence of SEQ ID NO: 1; H-CDR2 having the amino acid sequence of SEQ ID NO: 3; and H-CDR3 having any one selected from the group consisting of the amino acid sequences of SEQ ID NOs: 5, 7, and 9; and a light chain variable region (VL) that includes L-CDR1 having the amino acid sequence of SEQ ID NO: 2; L-CDR2 having the amino acid sequence of SEQ ID NO: 4; and L-CDR3 having any one selected from the group consisting of the amino acid sequences of SEQ ID NOs: 6, 8, 10, and 11. Preferably, the first domain may include a heavy chain variable region (VH) that includes H-CDR1 having the amino acid sequence of SEQ ID NO: 1; H-CDR2 having the amino acid sequence of SEQ ID NO: 3; and H-CDR3 having the amino acid sequence of SEQ ID NO: 7; and a light chain variable region (VL) that includes L-CDR1 having the amino acid sequence of SEQ ID NO: 2; L-CDR2 having the amino acid sequence of SEQ ID NO: 4; and L-CDR3 having the amino acid sequence of SEQ ID NO: 8.

In an embodiment of the present invention, a first monomer obtained by binding the C-terminus of the first domain to the N-terminus of the Fc region may have a heavy chain having any one selected from the group consisting of the amino acid sequences of SEQ ID NOs: 12, 14, 16, and 17; and a light chain having any one selected from the group consisting of the amino acid sequences of SEQ ID NO: 13, 15, 18, and 19.

In an embodiment of the present invention, the second domain may have the amino acid sequence of SEQ ID NO: 21. In an embodiment of the present invention, the fusion protein may have a structure in which the C-terminus of the second domain is bound to the N-terminus of the Fc region;

and a second monomer obtained by the above-mentioned binding may have the amino acid sequence of SEQ ID NO: 20.

More specifically, the first domain and the Fc region may be bound to each other via a linker. In addition, the second domain and the Fc region may be bound to each other via a linker. As the linker, a single-chain peptide linker, which consists of 5 to 20 amino acids joined together by peptide bonds, may be used. The amino acids may be one or more selected from the group consisting of glycine, serine, alanine, proline, valine, leucine, isoleucine, methionine, phenylalanine, tyrosine, tryptophan, threonine, cysteine, asparagine, glutamine, lysine, arginine, histidine, aspartic acid, and glutamic acid. Specifically, the linker may consist of glycine and serine, and may be a linker of (G4S)n (where n is 1 to 5). In an embodiment of the present invention, the linker may have the amino acid sequence of SEQ ID NO: 22.

In an embodiment of the present invention, the fusion protein may have an asymmetric structure in which the C-terminus of the first domain is bound to the N-terminus of either one of the dimeric Fc region, and the C-terminus of the second domain is bound to the other N-terminus of the dimeric Fc region. Since the fusion protein has an asymmetric structure, it is possible to prevent a problem that a divalent antibody is likely to be biased toward a degradation pathway.

In an embodiment of the present invention, the fusion protein may be a human antibody, a humanized antibody, or a chimeric antibody. The term "human antibody" refers to an intact antibody having a variable region whose structure and CDR regions are derived from an immunoglobulin sequence; the term "humanized antibody" refers to a chimeric antibody that includes a minimal sequence derived from an immunoglobulin of a non-human antibody such as a mouse antibody; and the term "chimeric antibody" refers to an antibody derived from a combination of different mammals such as mouse, rat, rabbit, goat, or human.

In an embodiment of the present invention, the fusion protein may be prepared by methods commonly practiced in the art, for example, knob-in-hole method (Ridgway et al, Protein Engineering, 617-621 (1996)), phage antibody library method (Clackson et al, Nature, 352:624-628 (1991)), fusion method (Kohler and Milstein, European Journal of Immunology, 6:511-519 (1976)), and recombinant DNA method (U.S. Pat. No. 4,816,567).

In an embodiment of the present invention, IDS-fused fusion proteins (IDS-IR739, IDS-HL009, and IDS-H031) were prepared using the phage antibody library method and the knob-in-hole method. The fusion proteins can bind to an insulin receptor and pass through the BBB via a receptor-mediated transcytosis (RMT) mechanism, so that an IDS-fused fusion partner site can act on a target in the brain (FIG. 1).

For antibodies that pass through the BBB via the RMT mechanism, their affinity for a BBB receptor is very important. Specifically, in a case where the affinity is lower than an appropriate level, there is a problem that their binding efficiency to the BBB is decreased. On the other hand, in a case where the affinity is higher than the appropriate level, a rate at which a therapeutic agent is released after passing through the BBB is deceased, resulting in a decrease in BBB passage efficiency.

In an embodiment of the present invention, the fusion protein may not inhibit binding of insulin to an insulin receptor.

In addition, in an aspect of the present invention, there is provided a pharmaceutical composition for preventing or treating a central nervous system (CNS) disease, comprising the fusion protein as an active ingredient.

The term "central nervous system (CNS)", as used herein, refers to a complex of nervous tissues which controls body functions, and includes the brain and the spinal cord. The central nervous system disease refers to a disease or disorder which affects the CNS and/or has an etiology in the CNS. Specific examples of the disease include lysosome storage disease (LSD), Huntington's disease, epilepsy, Parkinson's disease, Alzheimer's disease, stroke, corticobasal degeneration (CBD), corticobasal ganglionic degeneration (CBGD), frontotemporal dementia (FTD), multiple system atrophy (MSA), progressive supranuclear palsy (PSP), and brain cancer. Specific examples of the lysosomal storage disease include Hunter syndrome, Tay-Sachs disease, Niemann-Pick disease, Pompe disease, Krabbe disease, 'Gaucher disease, Fabry disease, Wolman disease, Morquio syndrome, Menkes syndrome, galactosialidosis, glycogen storage disease, Fanconi-Bickel syndrome, Lesch-Nyhan syndrome, Zellweger syndrome, and the like.

The pharmaceutical composition may further comprise a pharmaceutically acceptable carrier. For oral administration, a binder, a lubricant, a disintegrant, an excipient, a solubilizer, a dispersant, a stabilizer, a suspending agent, a coloring agent, a flavoring agent, and the like may be used. For injections, a buffering agent, a preservative, a soothing agent, a solubilizer, an isotonic agent, a stabilizer, and the like may be mixed and used. For topical administration, a base, an excipient, a lubricant, a preservative, and the like may be used.

The pharmaceutical composition may be prepared in various formulations by being mixed with the above-described pharmaceutically acceptable carrier. For injections, the pharmaceutical composition may be prepared in unit dosage ampoules or multiple dosage forms.

In addition, the pharmaceutical composition may comprise a surfactant capable of enhancing membrane permeability thereof. This surfactant includes, but is not limited to, those derived from steroids, cationic lipids such as N-[1-(2, 3-dioleoyl)propyl-N,N,N-trimethylammoniumchloride (DOTMA), or various compounds such as cholesterol hemisuccinate and phosphatidyl glycerol.

For administration route and dosage of the pharmaceutical composition, administration may be performed in various ways and amounts depending on the individual's condition and the presence or absence of adverse effects, and the optimal administration method and dosage may be selected in an appropriate range by a person skilled in the art.

Specifically, for parenteral administration, the pharmaceutical composition may be administered by any one route selected from, but not limited to, the group consisting of intravenous, intramuscular, intradermal, subcutaneous, intraperitoneal, intraarteriolar, intraventricular, intralesional, intrathecal, and topical administration, and combinations thereof. In addition, a daily dosage of the composition is about 0.0001 mg/kg to 100 mg/kg, and preferably 0.001 mg/kg to 10 mg/kg; and the dosage is preferably administered once to several times a day. However, the dosage may vary depending on the individual's body weight, age, gender, health status, diet, administration time, administration method, excretion rate, and severity of disease.

The pharmaceutical composition may be administered in various formulations when administered parenterally; and in a case of being prepared into formulations, the pharmaceutical composition may be prepared using commonly used diluents or excipients, such as fillers, extenders, binders, wetting agents, disintegrants, and surfactants. Formulations for parenteral administration may include sterilized aqueous solutions, non-aqueous solutions, suspensions, emulsions, lyophilized formulations, and suppositories. In addition, for the non-aqueous solutions or suspensions, vegetable oils such as propylene glycol, polyethylene glycol, and olive oil, injectable esters such as ethyl oleate, and the like may be used. For a base of the suppositories, Witepsol, Macrogol, Tween 61, cacao butter, laurin fat, glycerogelatin, or the like may be used.

The term "individual", as used herein, refers to a mammal, preferably a human, suffering from or at risk of developing a condition or disease that can be alleviated, suppressed, or treated by administration of the pharmaceutical composition.

The term "prevention", as used herein, refers to any act of blocking a disease, or suppressing or delaying symptoms of the disease using the pharmaceutical composition.

The term "treatment", as used herein, refers to any act of improving or beneficially altering a disease using the pharmaceutical composition.

In addition, in an aspect of the present invention, there is provided a method for preparing a fusion protein, comprising steps of: causing an antibody binding to an insulin receptor to be bound to an Fc region, to prepare a first monomer; causing iduronate-2-sulfatase (IDS) to be bound to a heterodimeric Fc region, to prepare a second monomer; and mixing the first monomer with the second monomer.

In an embodiment of the present invention, the Fc region may be derived from the heavy chain constant region (CH) of IgG1, IgG2, IgG3, or IgG4.

In an embodiment of the present invention, the antibody may include a heavy chain variable region (VH) that includes H-CDR1 having the amino acid sequence of SEQ ID NO: 1; H-CDR2 having the amino acid sequence of SEQ ID NO: 3; and H-CDR3 having any one selected from the group consisting of the amino acid sequences of SEQ ID NOs: 5, 7, and 9; and a light chain variable region (VL) that includes L-CDR1 having the amino acid sequence of SEQ ID NO: 2; L-CDR2 having the amino acid sequence of SEQ ID NO: 4; and L-CDR3 having any one selected from the group consisting of the amino acid sequences of SEQ ID NOs: 6, 8, 10, and 11. Specifically, the antibody fragment may include a heavy chain variable region (VH) that includes H-CDR1 having the amino acid sequence of SEQ ID NO: 1; H-CDR2 having the amino acid sequence of SEQ ID NO: 3; and H-CDR3 having the amino acid sequence of SEQ ID NO: 7; and a light chain variable region (VL) that includes L-CDR1 having the amino acid sequence of SEQ ID NO: 2; L-CDR2 having the amino acid sequence of SEQ ID NO: 4; and L-CDR3 having the amino acid sequence of SEQ ID NO: 8.

In an embodiment of the present invention, in a case where CH3 in the Fc region of the first monomer has a knob structure, CH3 in the second monomer may have a hole structure; or in a case where CH3 in the Fc region of the first monomer has a hole structure, CH3 in the second monomer may have a knob structure.

In an embodiment of the present invention, the IDS may have the amino acid sequence of SEQ ID NO: 21.

In an embodiment of the present invention, the first monomer may include a heavy chain having any one selected from the group consisting of the amino acid sequences of SEQ ID NOs: 12, 14, 16, and 17, and a light chain having any one selected from the group consisting of the amino acid sequences of SEQ ID NO: 13, 15, 18, and 19; and the second monomer may have the amino acid sequence of SEQ ID NO: 20.

More specifically, the fusion protein IDS-IR739 according to the present invention may comprise a first monomer that includes a heavy chain having the amino acid sequence of SEQ ID NO: 12 or 16 and a light chain having the amino acid sequence of SEQ ID NO: 13, and a second monomer having the amino acid sequence of SEQ ID NO: 20.

The fusion protein IDS-HL009 according to the present invention may comprise a first monomer that includes a heavy chain having the amino acid sequence of SEQ ID NO: 14 and a light chain having the amino acid sequence of SEQ ID NO: 15, and a second monomer having the amino acid sequence of SEQ ID NO: 20.

The fusion protein IDS-H031 according to the present invention may comprise a first monomer that includes a heavy chain having the amino acid sequence of SEQ ID NO: 14 and a light chain having the amino acid sequence of SEQ ID NO: 13, and a second monomer having the amino acid sequence of SEQ ID NO: 20.

The fusion protein IDS-H118 according to the present invention may comprise a first monomer that includes a heavy chain having the amino acid sequence of SEQ ID NO: 17 and a light chain having the amino acid sequence of SEQ ID NO: 13, and a second monomer having the amino acid sequence of SEQ ID NO: 20.

The fusion protein IDS-L016 according to the present invention may comprise a first monomer that includes a heavy chain having the amino acid sequence of SEQ ID NO: 12 or 16 and a light chain having the amino acid sequence of SEQ ID NO: 18, and a second monomer having the amino acid sequence of SEQ ID NO: 20.

The fusion protein IDS-L113 according to the present invention may comprise a first monomer that includes a heavy chain having the amino acid sequence of SEQ ID NO: 12 or 16 and a light chain having the amino acid sequence of SEQ ID NO: 19, and a second monomer having the amino acid sequence of SEQ ID NO: 20.

The present invention provides a use of the fusion protein for preventing or treating a central nervous system disease.

In addition, the present invention provides a use of the fusion protein for manufacture of a medicament for preventing or treating a central nervous system disease.

In addition, the present invention provides a method for preventing or treating a central nervous system disease, and/or a method for enhancing a therapeutic effect, the method comprising a step of administering, to an individual, the fusion protein or the pharmaceutical composition comprising the fusion protein.

The individual may be an individual suffering from a central nervous system disease. In addition, the individual may be a mammal, and preferably a human.

For administration route, dosage, and administration frequency of the fusion protein or the pharmaceutical composition, administration to a subject may be performed in various ways and amounts depending on the subject's condition and the presence or absence of adverse effects, and the optimal administration method, dosage, and administration frequency may be selected in an appropriate range by a person skilled in the art. In addition, the fusion protein or the pharmaceutical composition may be administered in combination with other drugs or physiologically active substances whose therapeutic effect is known for the disease to be treated, or may be formulated in the form of a combination formulation with other drugs.

MODE FOR THE INVENTION

Hereinafter, the present invention will be described in more detail by way of the following examples. However, the following examples are for illustrative purposes only, and the scope of the present invention is not limited thereto.

Preparation Example 1. Preparation of IR739 Antibody

Human synthetic scFv libraries (MIDAS, MOGAM) were used to prepare anti-IR antibodies. A phage library of MIDAS was placed in a tube coated with human IR at a concentration of 5 μg/ml, and treatment was performed at 37° C. for 2 hours. Washing was performed 4 times with PBS buffer to which 0.05% Tween 20 was added. Then, treatment with 1% BSA/0.1 M glycine (pH 2.0) buffer was performed at room temperature for 10 minutes to elute phages bound to IR. The eluted phages were neutralized with 70 μl of 2 M Tris-HCl (pH 9.0), and used to infect 9 ml of previously cultured E. coli (XL1-Blue) for 30 minutes. To the phage-infected XL1-Blue were added super broth (SB) medium, tetracycline, and carbenicillin, and culture was performed at 37° C. for 1 hour. Then, helper phages were added thereto. Culture was performed for additional one hour. The medium was added thereto up to 100 ml, and culture was performed overnight at 37° C.

The culture medium was harvested by centrifugation, and the phages were precipitated with a 20% PEG solution. After centrifugation, the phages were collected with a PBS solution to which 1% BSA was added. Using the solution in which the phages were collected, a panning process was repeated up to the fourth time alternately with a mouse IR-coated tube and a human IR-coated tube. Each of tertiary phage- and quaternary phage-infected XL1-Blue colonies was cultured, to obtain each phage-containing culture solution. Using the culture solution and IR-coated plates, phage-expressing XL1-Blue clones that simultaneously bind to human IR and mouse IR were selected by ELISA. Plasmids of the selected clones were sequenced to obtain VH and VL sequences. Based on these sequences, antibodies having a conventional IgG form were prepared.

Through the cross-reactivity evaluation in Experimental Example 1 below, among the antibodies obtained through screening of the MIDAS human scFv libraries, IR739, which is an antibody binding to both human IR, monkey IR, and mouse IR, was selected. A protein sequence of IR739 prepared as described above is shown in Table 1 below.

TABLE 1

| | |
|---|---|
| H-chain | EVQLVESGGGLVQPGGSLRLSCAASGFTFSSYYMSWVRQAPGK GLEWVSAISYGGSSTYYADSVKGRFTISRDNSKNTLYLQMNSL RAEDTAVYYCARHPSYGTVNHAYFDVWGQGTLVTVSSASTKGP SVFPLAPSSKSTSGGTAALGCLVKDYFPEPVTVSWNSGALTSG VHTFPAVLQSSGLYSLSSVVTVPSSSLGTQTYICNVNHKPSNT KVDKKVEPKSCDKTHTCPPCPAPELLGGPSVFLFPPKPKDTLM ISRTPEVTCVVVDVSHEDPEVKFNWYVDGVEVHNAKTKPREEQ YNSTYRVVSVLTVLHQDWLNGKEYKCKVSNKALPAPIEKTISK AKGQPREPQVYTLPPSRDELTKNQVSLTCLVKGFYPSDIAVEW ESNGQPENNYKTTPPVLDSDGSFFLYSKLTVDKSRWQQGNVFS CSVMHEALHNHYTQKSLSLSPG (SEQ ID NO: 12) |
| L-chain | DIQMTQSPSSLSASVGDRVTITCGASRDVSSYLAWYQQKPGKA PKLLIYDANILQSGVPSRFSGSGSGTDFTLTISSLQPEDFATY YCLEYNNLPLTFGQGTKVEIKRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC (SEQ ID NO: 13) |

Preparation Example 2. Preparation of Variants of IR739 Antibody

Figure 2:
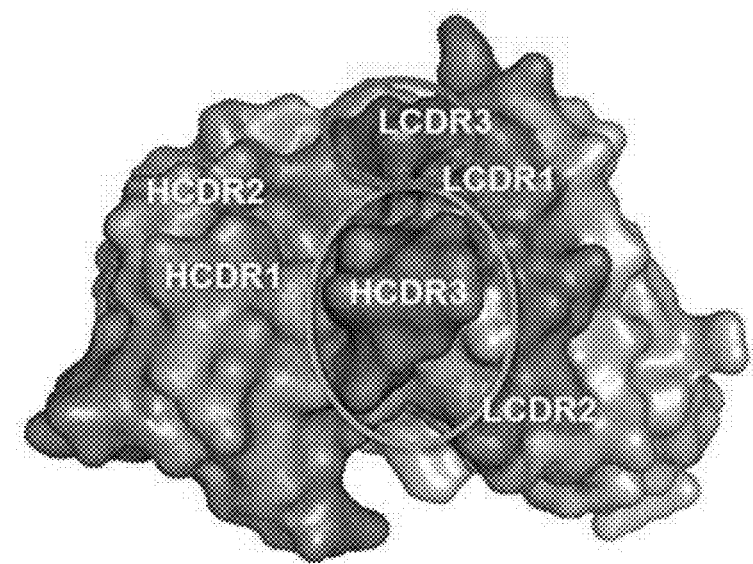
FIG. 2 illustrates mutation-introduced sites in an antibody (IR739) binding to an insulin receptor.

Using random mutagenesis, mutations were introduced into the Asn-Asn sequence in LCDR3 and the Ser-Tyr-Gly-Thr-Val-Asn-His sequence in HCDR3 (FIG. 2). In order to introduce the mutations, the gene of IR739 was subjected to PCR using primers obtained by replacing codons of the corresponding sequences with NNK degenerate codons (N=A, T, G, or C, and K=G or T), to prepare mutant scFv DNA fragments. 1 μg of pCIw vector (Promega), to which each of the mutant scFv DNA fragments was ligated, was transformed into 100 μl of XL1-Blue by electroporation. Then, the resultant was placed in 10 ml of super broth (SB) medium, and culture was performed at 37° C. for 1 hour.

10 ml of helper phages were added thereto, and culture was performed at 37° C. for 1 hour. Then, 80 ml of medium supplemented with tetracycline and carbenicillin was further added thereto, and culture was performed overnight. The culture solution of XL1-Blue into which the mutations were introduced was harvested by centrifugation, and the phages were precipitated with a 20% PEG solution. After centrifugation, culture with 1% BSA/0.1 M glycine (pH 2.0) buffer was performed at room temperature for 10 minutes to elute phages bound to IR. The eluted phages were neutralized with 70 μl of 2 M Tris-HCl (pH 9.0), and used to infect 9 ml of previously cultured E. coli (XL1-Blue) for 30 minutes. To the phage-infected XL1-Blue were added super broth (SB) medium, tetracycline, and carbenicillin, and culture was performed at 37° C. for 1 hour. Then, helper phages were added thereto. Culture was performed for additional one hour. The medium was added thereto up to 100 ml, and culture was performed overnight at 37° C.

The culture medium was harvested by centrifugation, and the phages were precipitated with a 20% PEG solution. After centrifugation, the phages were collected with a PBS solution to which 1% BSA was added. Using the solution in which the phages were collected, a panning process was repeated up to the fourth time alternately with a mouse IR-coated tube and a human IR-coated tube. Each of tertiary phage- and quaternary phage-infected XL1-Blue colonies was cultured, to obtain each phage-containing culture solution. Using the culture solution and IR-coated plates, clones having higher or smaller absorbance than IR739 were selected through ELISA. The selected clones were sequenced to select unique sequences (FIG. 3), and cloned to prepare H031, H118, HL009, L016, and L113, which are variants having a conventional IgG form.

Preparation Example 3. Preparation of Asymmetric Fusion Antibodies

To prepare each of IDS fusion antibodies (IDS-IR739, IDS-H031, IDS-HL009, and IDS-8D3) in which one Fab was replaced with IDS, a knob-in-hole was introduced into the heavy chain of an immunoglobulin. In the heavy chain into which a knob was introduced, Lys409 was replaced with Trp409; and in the heavy chain into which a hole was introduced, Asp399 and Phe405 were replaced with Val399 and Thr405, respectively. Through cloning, the VH in IR739, HL009, and 8D3 was replaced with the VH of the heavy chain into which the hole was introduced, and the C-terminus of IDS was fused to the N-terminus of CH2 of the heavy chain into which the knob was introduced. The 8D3, which is an antibody against a transferrin receptor, was used as a control.

A plasmid expressing the light chain and the heavy chain into which the hole was introduced, and a plasmid expressing CH2-CH3 into which the knob was introduced and to which IDS was fused were co-transfected into CHO cells. Culture was performed at 37° C. for 10 days. The culture solution was separated by centrifugation. Then, IDS-IR739, IDS-HL009, IDS-H031, and IDS-8D3 were purified with a Protein A column. The IDS fusion antibody was eluted from the Protein A column using 1 M L-arginine solution (pH 4). A structure of the asymmetric fusion antibody prepared as described above is illustrated in FIG. 1 (left).

Experimental Example 1. Cross-Reactivity Evaluation

Figure 4:
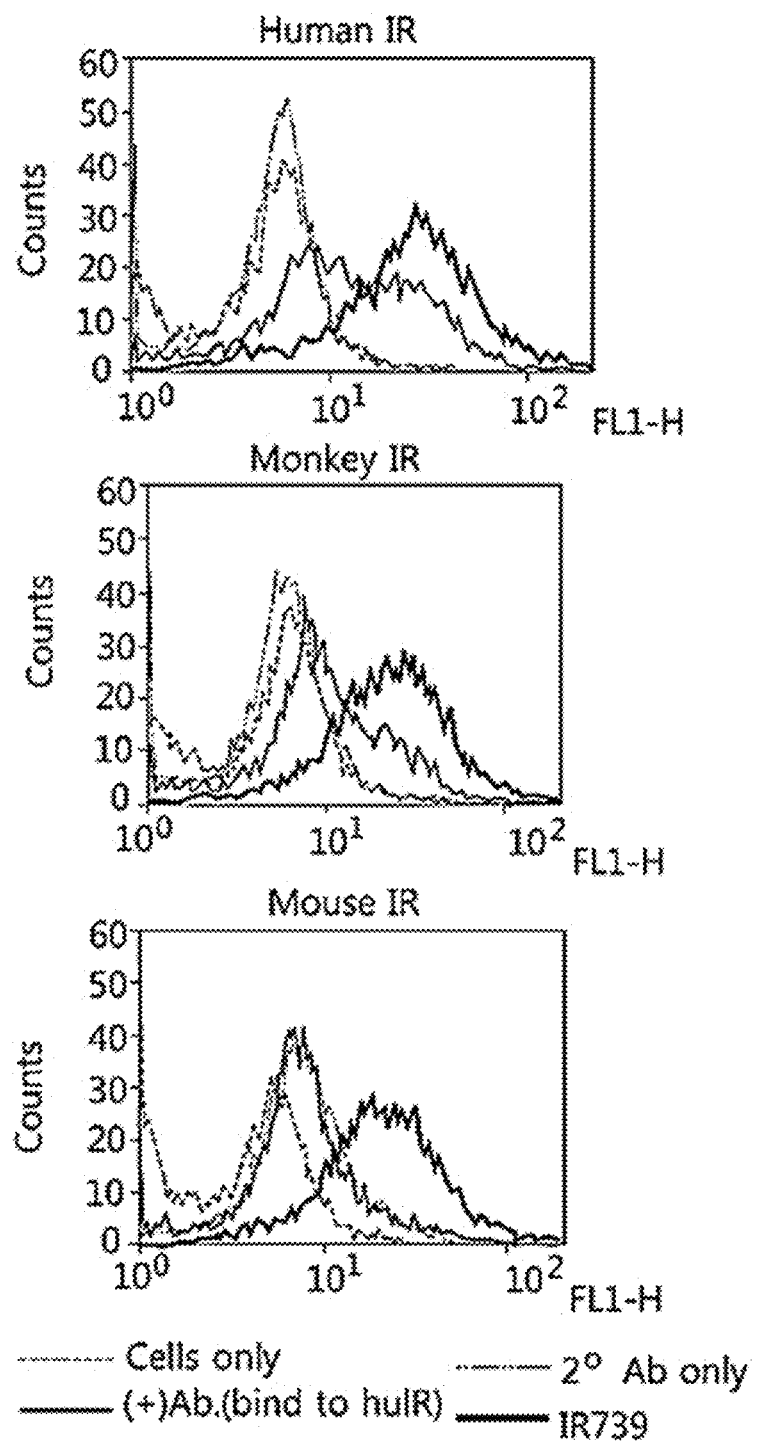
FIG. 4 illustrates results obtained by performing FACS analysis for evaluating cross-reactivity of IR739 in a human, a monkey, and a mouse.

Respective Expi-293 cells, in which each of human IR, monkey IR, and mouse IR was overexpressed, were harvested, and placed in respective tubes at $5 \times 10^6$ cells/ml. Then, the tubes were treated with 1 µg/ml of each of the antibodies obtained through screening of the MIDAS human scFv libraries. Culture was performed at 4° C. for 30 minutes, and then washing was performed 3 times with cold PBS using a centrifuge. A fluorochrome-labeled anti-human antibody (FITC-conjugated anti-human IgG) in 3% BSA/PBS buffer was added thereto, and culture was performed at 4° C. for 30 minutes in the dark. Washing was performed 3 times with a cold buffer of 3% BSA/1% sodium azide/PBS using a centrifuge. Analysis was performed using a FACS instrument. As a result, it was identified that the antibody IR739 bound to all of the human IR, the monkey IR, and the mouse IR (FIG. 4).

Experimental Example 2. Evaluation of Binding Affinity to IR

Experimental Example 2.1. Evaluation of Binding Affinity of IR739

The binding affinity of IR739 to IR was analyzed through surface plasmon resonance (SPR). Human IR or mouse IR at 1 µg/ml was immobilized with acetate (pH 4.0) on a CM5 sensor chip. IR739 was flowed, at a concentration of 100 nM, 50 nM, 25 nM, 12.5 nM, 6.25 nM, 3.125 nM, or 1.563 nM, over the CM5 sensor chip to which the human IR or the mouse IR was immobilized, while measuring association and dissociation thereof. For measurement conditions, a flow rate was set as 30 µl/min, and an association time and a dissociation time were set as 120 seconds and 600 seconds, respectively. For regeneration, 10 mM glycine-HCl (pH 1.5) was flowed for 30 seconds. The results of the binding affinity of IR739 to the human IR and the mouse IR are shown in Table 2 below.

TABLE 2

| pH 7.0 | Ka (/Ms) | Kd (/s) | KD (M) |
| --- | --- | --- | --- |
| Human IR | $9.595 \times 10^4$ | $14.35 \times 10^{-4}$ | $14.96 \times 10^{-9}$ |
| Mouse IR | $9.532 \times 10^4$ | $6.100 \times 10^{-4}$ | $6.4 \times 10^{-9}$ |

Experimental Example 2.2. Comparison of Binding Affinity of IR739 and Variants of IR739

ELISA was performed to compare the binding affinity of IR739 and variants thereof to IR. An ELISA plate coated with IR at a concentration of 5 µg/ml was blocked with 3% skim milk for 1 hour, and then respective wells were treated with IR739 and the variants thereof at various concentrations. Treatment was performed at 37° C. for 1 hour, and then washing was performed 3 times with 0.05% Tween 20/PBS solution. To detect IR739 and the variants thereof, treatment with peroxidase-conjugated anti-human Fc IgG was performed, and incubation was performed at 37° C. for 1 hour. Then, washing was performed 3 times with 0.05% Tween 20/PBS solution. Color development was performed with tetramethylbenzidine (TMB) ELISA solution, and absorbance at 450 nm was analyzed. As a result, H031 and HL009 had higher binding affinity to the human IR and the mouse IR than IR739, and L016 and H118 had lower binding affinity thereto than IR739. L113 exhibited similar binding affinity to IR739 (FIG. 5).

Experimental Example 2.3. Evaluation of Binding Affinity of Asymmetric Fusion Antibodies ELISA was performed to identify the binding affinity of IDS-HL009 to IR. An ELISA plate coated with IR at a concentration of 5 µg/ml was blocked with 3% skim milk for 1 hour, and then respective wells were treated with IR739, IDS-IR739, IDS-HL009, or IDS-H031 at various concentrations. Treatment was performed at 37° C. for 1 hour, and then washing was performed 3 times with 0.05% Tween 20/PBS solution. To detect IR-739, IDS-IR739, IDS-HL009, and IDS-H031, treatment with peroxidase-conjugated anti-human Fc IgG was performed, and incubation was performed at 37° C. for 1 hour. Then, washing was performed 3 times with 0.05% Tween 20/PBS solution. Color development was performed with TMB ELISA solution, and absorbance at 450 nm was analyzed. As a result, IDS-IR739, IDS-H031, and IDS-HL009 had lower binding affinity to the human IR and the mouse IR than IR739 because in such antibodies, an avidity effect was eliminated by replacement of one Fab with IDS (FIG. 6).

Experimental Example 3. Identification of Competition Between Insulin and IR739 for IR To identify interaction between IR739 and insulin on IR, competitive ELISA was performed. An ELISA plate coated with IR at a concentration of 5 µg/ml was blocked with 3% skim milk for 1 hour. Then, to respective wells was added a mixture of IR739 and biotinylated insulin at various concentrations. Incubation was performed at 37° C. for 1 hour, and then washing was performed 3 times with 0.05% Tween 20/PBS solution. Treatment with peroxidase-conjugated anti-human Fc IgG was performed to detect IR739, and treatment with peroxidase-conjugated streptavidin was performed to detect the biotinylated insulin.

Incubation was performed at 37° C. for 1 hour. Then, washing was performed 3 times with 0.05% Tween 20/PBS solution, and color development was performed with TMB ELISA solution. Absorbance at 450 nm was analyzed. As a result, a binding pattern of IR739 to IR was not affected by changes in insulin concentration. Specifically, while the insulin concentration changed from 0.6 nM to 150 nM, no changes were observed in binding curves for respective concentrations of IR739 (FIG. 7). In addition, a binding pattern of insulin to IR was also not affected by changes in IR739 concentration; and specifically, no changes were observed in binding curves for respective insulin concentrations while the IR739 concentration changed from 0.03 nM to 7 nM (FIG. 8).

Experimental Example 4. Evaluation of Pharmacokinetics in Mouse Blood

Experimental Example 4.1. Evaluation of Pharmacokinetics of IR739 in Mouse Blood To analyze stability of IR739 in mouse blood, 5 mg/kg of IR739 or 8D3 antibody (anti-TfR antibody), which was a control, was administered to the tail vein of each mouse. After administration, 50 µl of blood was collected by eye-bleeding at 30 minutes, 1 hour, 2 hours, 6 hours, and 24 hours, respectively. The blood was centrifuged, and an antibody concentration in the supernatant was analyzed by ELISA. For ELISA, an ELISA plate was coated with anti-human Fab IgG at 1 µg/ml, blocked with 3% skim milk, and then treated with 50 µl of the supernatant diluted 1/10. Incubation was performed at 37° C. for 1 hour, and then washing was performed 3 times with 0.05% Tween 20/PBS solution. Treatment with peroxidase-conjugated anti-human Fc IgG was performed. Treatment was performed at 37° C. for 1 hour. Then, washing was performed 3 times with 0.05% Tween 20/PBS solution, and detection was performed with TMB ELISA solution. The concentration was calculated using, as a standard, the results obtained by performing ELISA in the same manner as above with IR739 at 10,000 ng/ml to 4.5 ng/ml (10,000 ng/ml, 3,333 ng/ml, 1,111 ng/ml, 370 ng/ml, 123 ng/ml, 41.2 ng/ml, 13.7 ng/ml, 4.5 ng/ml). It was identified that IR739 had a half-life of about 24 hours (FIG. 9).

Experimental Example 4.2. Evaluation of Pharmacokinetics of IDS-HL009 in Mouse Blood To analyze stability of IDS-HL009 in mouse blood, 5 mg/kg of IDS, IR739, IDS-HL009, or IDS-8D3 was administered to the tail vein of each mouse. After administration, 50 µl of blood was collected by eye-bleeding at 30 minutes, 1 hour, 2 hours, 6 hours, and 24 hours, respectively. The blood was centrifuged, and an antibody concentration in the supernatant was analyzed by ELISA. For ELISA, an ELISA plate was coated with anti-human Fab IgG at 1 µg/ml, blocked with 3% skim milk, and then treated with 50 µl of the supernatant diluted 1/10.

Incubation was performed at 37° C. for 1 hour, and then washing was performed 3 times with 0.05% Tween 20/PBS solution. Treatment with peroxidase-conjugated anti-human Fc IgG was performed. Treatment was performed at 37° C. for 1 hour. Then, washing was performed 3 times with 0.05% Tween 20/PBS solution, and detection was performed with TMB ELISA solution. The concentration was calculated using, as a standard, the results obtained by performing ELISA in the same manner as above with IR739, IDS-HL009, and IDS-8D3 at 10,000 ng/ml to 4.5 ng/ml (10,000 ng/ml, 3,333 ng/ml, 1,111 ng/ml, 370 ng/ml, 123 ng/ml, 41.2 ng/ml, 13.7 ng/ml, 4.5 ng/ml). To measure the IDS concentration, ELISA was performed on an ELISA plate coated with anti-IDS IgG using biotin-conjugated anti-IDS and HRP-conjugated streptavidin. It was identified that IDS-HL009 had a half-life of about 14 hours (FIG. 10).

Experimental Example 5. Evaluation of Brain Uptake

Experimental Example 5.1. Evaluation of Brain Uptake Efficiency of IR739

Figure 11:
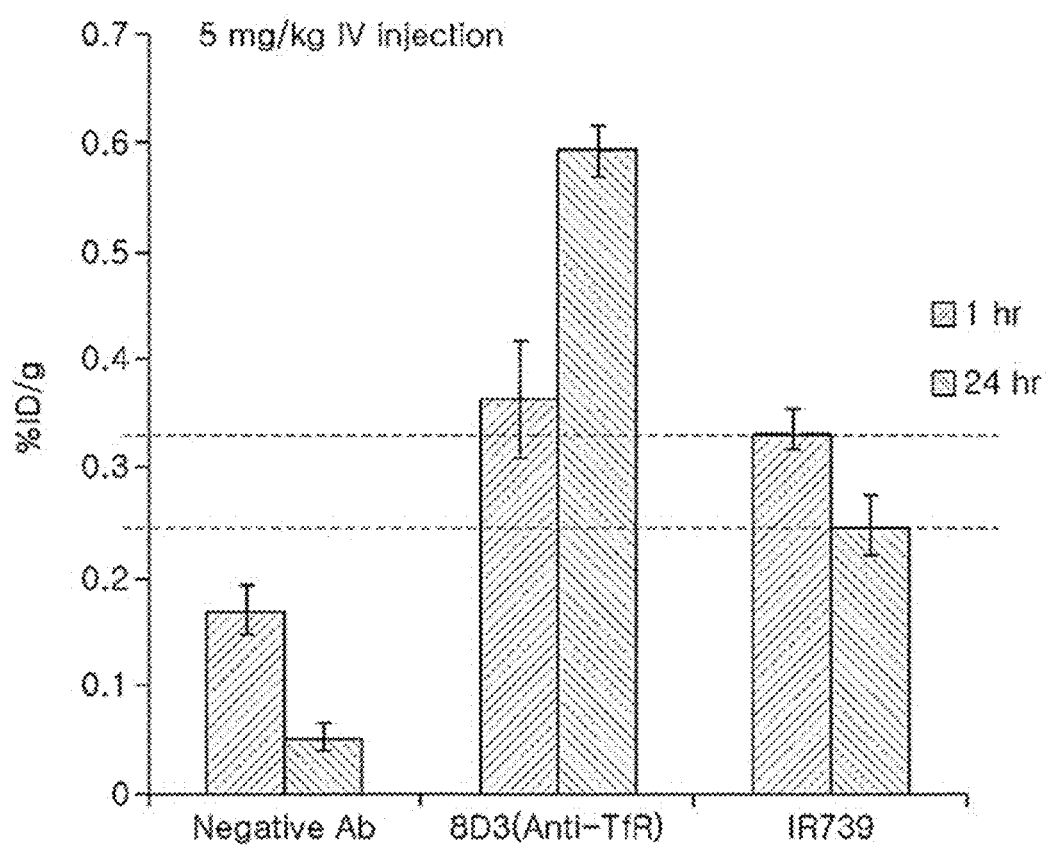
FIG. 11 illustrates brain uptake efficiency of IR739.

To analyze brain uptake efficiency of IR739, negative control IgG (anti-mesothelin (MSLN) IgG), 8D3, or IR739 at 5 mg/kg was injected into the tail vein of each mouse. Here, the anti-mesothelin IgG was used as a negative control and 8D3 was used as a positive control. After 1 hour and 24 hours, each of 3 mice for each substance was perfused, and then the brain was removed therefrom. 1 ml of lysis buffer was added per 100 mg of the brain, and pulverization was performed. Then, centrifugation was performed at 13,000 rpm. An ELISA plate was coated with anti-human Fab IgG at 1 µg/ml, blocked with 3% skim milk, and then treated with 50 µl of the supernatant. Incubation was performed at 37° C. for 1 hour, and then washing was performed 3 times with 0.05% Tween 20/PBS solution. Treatment with peroxidase-conjugated anti-human Fc IgG was performed. Incubation was performed at 37° C. for 1 hour. Then, washing was performed 3 times with 0.05% Tween 20/PBS solution, and detection was performed with TMB ELISA solution. The concentration was calculated using, as a standard, the results obtained by performing ELISA in the same manner as above with anti-MSLN IgG, 8D3, and IR739 at 1,000 ng/ml to 0.45 ng/ml (1,000 ng/ml, 333 ng/ml, 111 ng/ml, 37.0 ng/ml, 12.3 ng/ml, 4.12 ng/ml, 1.37 ng/ml, 0.45 ng/ml). IR739 exhibited lower brain uptake efficiency than 8D3 while exhibiting higher brain uptake efficiency than the anti-MSLN IgG (FIG. 11).

Experimental Example 5.2. Evaluation of Brain Uptake Efficiency of Variants of IR739

Figure 12:
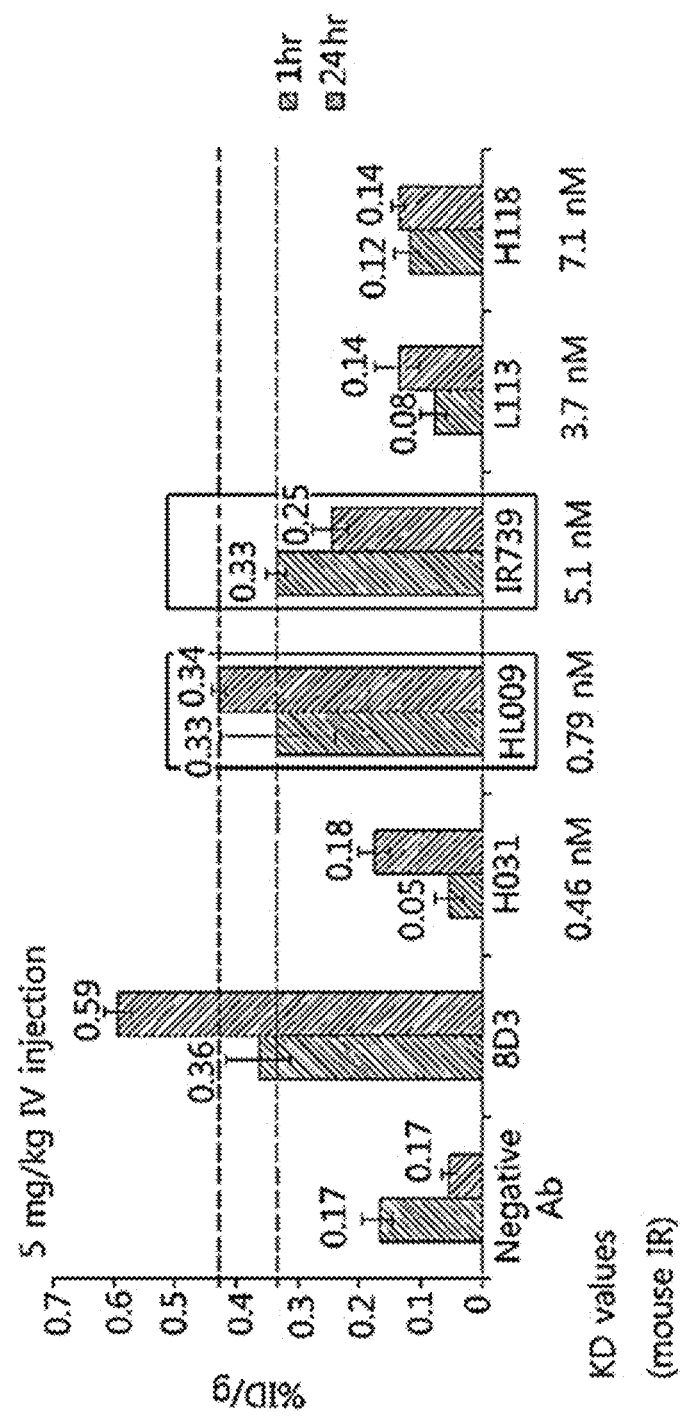
FIG. 12 illustrates results obtained by comparing brain uptake efficiency of variants of IR739 (H031, HL009, L113, and H118).

To analyze brain uptake efficiency of the variants of IR739, anti-MSLN IgG, 8D3, IR739, H031, HL009, L113, or H118 at 5 mg/kg was injected into the tail vein of each mouse. After 1 hour and 24 hours, each of 3 mice for each substance was perfused, and then the brain was removed therefrom. 1 ml of lysis buffer was added per 100 mg of the brain, and pulverization was performed. Then, centrifugation was performed at 13,000 rpm. An ELISA plate was coated with anti-human Fab IgG at 1 g/ml, blocked with 3% skim milk, and then treated with 50 µl of the supernatant. Incubation was performed at 37° C. for 1 hour, and then washing was performed 3 times with 0.05% Tween 20/PBS solution. Treatment with peroxidase-conjugated anti-human Fc IgG was performed. Incubation was performed at 37° C. for 1 hour. Then, washing was performed 3 times with 0.05% Tween 20/PBS solution, and detection was performed with TMB ELISA solution. The concentration was calculated using, as a standard, the results obtained by performing ELISA in the same manner as above with anti-MSLN IgG, 8D3, IR739, H031, HL009, L113, and H118 at 1,000 ng/ml to 0.45 ng/ml (1,000 ng/ml, 333 ng/ml, 111 ng/ml, 37.0 ng/ml, 12.3 ng/ml, 4.12 ng/ml, 1.37 ng/ml, 0.45 ng/ml). As a result of the analysis, among the variants, HL009 exhibited higher brain uptake efficiency than IR739, whereas H031, L113, and H118 exhibited lower brain uptake efficiency than IR739 (FIG. 12).

Experimental Example 5.3. Evaluation of Brain Uptake Efficiency of IDS-HL009

Figure 13:
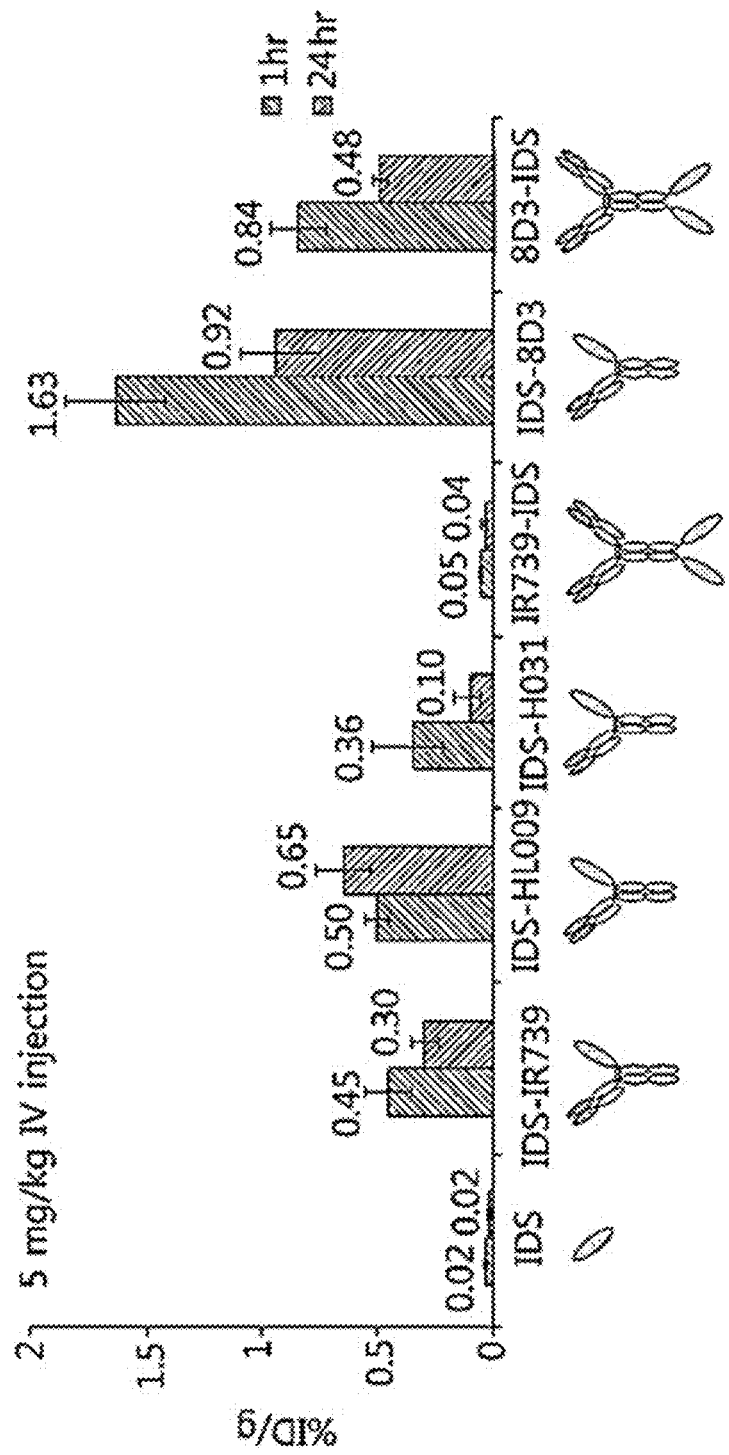
FIG. 13 illustrates results obtained by comparing brain uptake efficiency of fusion proteins.

To analyze brain uptake efficiency of IDS-HL009, IDS-HL009 at 5 mg/kg was injected into the tail vein of each mouse. After 1 hour and 24 hours, each of 3 mice for each substance was perfused, and then the brain was removed therefrom. 1 ml of lysis buffer was added per 100 mg of the brain, and pulverization was performed. Then, centrifugation was performed at 13,000 rpm. An ELISA plate was coated with anti-human Fab IgG at 1 µg/ml, blocked with 3% skim milk, and then treated with 50 µl of the supernatant. Incubation was performed at 37° C. for 1 hour, and then washing was performed 3 times with 0.05% Tween 20/PBS solution. Treatment with peroxidase-conjugated anti-human Fc IgG was performed. Incubation was performed at 37° C. for 1 hour. Then, washing was performed 3 times with 0.05% Tween 20/PBS solution, and detection was performed with TMB ELISA solution. The concentration was calculated using, as a standard, the results obtained by performing ELISA in the same manner as above with IDS-HL009 at 1,000 ng/ml to 0.45 ng/ml (1,000 ng/ml, 333 ng/ml, III ng/ml, 37.0 ng/ml, 12.3 ng/ml, 4.12 ng/ml, 1.37 ng/ml, 0.45 ng/ml). IDS-HL009 exhibited higher brain uptake efficiency than IDS, IDS-IR739, and IDS-H031 (FIG. 13).

Experimental Example 6. Evaluation of Characteristics of IDS-HL009

To analyze characteristics of IDS and IDS-HL009, 10 ng/ml IDS or 10 μl of IDS-HL009 and 20 μl of 100 mM 4-methylumbelliferyl α-L-idopyranosiduronic acid-2-sulfate (4MU-α-IdopyraA-2) were placed in a 96-well plate (black), and incubation was performed at 37° C. for 4 hours. The reaction was stopped by addition of 20 μl of a Pi/Ci solution (pH 4.5), and 10 μl of 25 μg/ml recombinant human α-L-iduronidase was added thereto. Incubation was performed at 37° C. for 24 hours. Then, 200 μl of 0.25 M sodium carbonate/bicarbonate (pH 10.0) was added thereto and fluorescence was measured (absorption: 355 nm/emission: 460 nm). The activity was analyzed using 4-methylumbelliferone as a standard, and the results are shown in Table 3 below.

TABLE 3

|  | IDS | IDS-HL009 |
| --- | --- | --- |
| nmol/min/μg | 51.4 | 13.0 |
| nmol/min/pmole | 3,084 | 2,105 |
| % of IDS |  | 68.3 |

As shown in Table 3, IDS activity of IDS-HL009 indicated IDS:IDS-HL009=51.4:13.0 nmol/min based on μg of protein, and indicated IDS:IDS-HL009=3,084:2,105 nmol/min based on mole of protein. From the above results, it was identifiable that IDS-HL009 had about 70% IDS activity with respect to IDS based on mole of protein.

The invention claimed is:

1. A fusion protein, comprising:
a first domain that includes a fragment of an antibody that binds to an insulin receptor; and
a second domain comprising iduronate-2-sulfatase (IDS), wherein the first domain comprises:
a heavy chain variable region (VH) that includes H-CDR1 comprising the amino acid sequence of SEQ ID NO: 1; H-CDR2 comprising the amino acid sequence of SEQ ID NO: 3; and H-CDR3 comprising any one selected from the group consisting of the amino acid sequences of SEQ ID NOs: 5, 7, and 9; and
a light chain variable region (VL) that includes L-CDR1 comprising the amino acid sequence of SEQ ID NO: 2; L-CDR2 comprising the amino acid sequence of SEQ ID NO: 4; and L-CDR3 comprising any one selected from the group consisting of the amino acid sequences of SEQ ID NOs: 6, 8, 10, and 11.

2. The fusion protein of claim 1, further comprising: an Fc region.

3. The fusion protein of claim 2, wherein the Fc region is heterodimeric.

4. The fusion protein of claim 3, wherein one of the heterodimeric Fc has a knob structure, and the other has a hole structure.

5. The fusion protein of claim 2, wherein the Fc region is derived from the heavy chain constant region (CH) of IgG1, IgG2, IgG3, or IgG4.

6. The fusion protein of claim 2, wherein the C-terminus of the first domain is bound to the N-terminus of the Fc region.

7. The fusion protein of claim 2, wherein the C-terminus of the second domain is bound to the N-terminus of the Fc region.

8. The fusion protein of claim 1, wherein the first domain is a Fab or scFv region of the antibody binding to an insulin receptor.

9. The fusion protein of claim 1, wherein the second domain comprises the amino acid sequence of SEQ ID NO: 21.

10. The fusion protein of claim 1, wherein the fusion protein does not inhibit binding between an insulin receptor and insulin.

11. A pharmaceutical composition comprising as an active ingredient:
the fusion protein of claim 1, and
a pharmaceutically acceptable carrier.

12. A method for treating an individual with a lysosomal storage disease, comprising:
administering, to the individual, a pharmaceutical composition of claim 11,
wherein the lysosomal storage disease is any one selected from the group consisting of Hunter syndrome, Tay-Sachs disease, Niemann-Pick disease, Pompe disease, Krabbe disease, Gaucher disease, Fabry disease, Wolman disease, Morquio syndrome, Menkes syndrome, galactosialidosis, glycogen storage disease, Fanconi-Bickel syndrome, Lesch-Nyhan syndrome, and Zellweger syndrome.

13. A method for preparing a fusion protein, comprising steps of:
causing a fragment of an antibody that binds to an insulin receptor to be bound to an Fc region, to prepare a first monomer;
causing iduronate-2-sulfatase (IDS) to be bound to a heterodimeric Fc region, to prepare a second monomer; and
mixing the first monomer with the second monomer,
wherein the antibody fragment comprises:
a heavy chain variable region (VH) that includes H-CDR1 comprising the amino acid sequence of SEQ ID NO: 1; H-CDR2 comprising the amino acid sequence of SEQ ID NO: 3; and H-CDR3 comprising any one selected from the group consisting of the amino acid sequences of SEQ ID NOs: 5, 7, and 9; and a light chain variable region (VL) that includes L-CDR1 comprising the amino acid sequence of SEQ ID NO: 2; L-CDR2 comprising the amino acid sequence of SEQ ID NO: 4; and L-CDR3 comprising any one selected from the group consisting of the amino acid sequences of SEQ ID NOs: 6, 8, 10, and 11.

14. The method of claim 13, wherein in a case where CH3 in the Fc region of the first monomer has a knob structure, CH3 in the second monomer has a hole structure; or in a case where CH3 in the Fc region of the first monomer has a hole structure, CH3 in the second monomer has a knob structure.

15. The method of claim 13, wherein the IDS has the amino acid sequence of SEQ ID NO: 21.

16. The method of claim 13, wherein the first monomer includes a heavy chain comprising any one selected from the group consisting of the amino acid sequences of SEQ ID NOs: 12, 14, 16, and 17, and a light chain comprising any one selected from the group consisting of the amino acid sequences of SEQ ID NO: 13, 15, 18, and 19, and the second monomer comprises the amino acid sequence of SEQ ID NO: 20.

* * * * *

SEQUENCE LISTING

```
<160> NUMBER OF SEQ ID NOS: 29

<210> SEQ ID NO 1
<211> LENGTH: 11
<212> TYPE: PRT
<213> ORGANISM: Artificial Sequence
<220> FEATURE:
<223> OTHER INFORMATION: H-CDR1 of fusion protein

<400> SEQUENCE: 1

Ser Gly Phe Thr Phe Ser Ser Tyr Tyr Met Ser
1               5                   10

<210> SEQ ID NO 2
<211> LENGTH: 11
<212> TYPE: PRT
<213> ORGANISM: Artificial Sequence
<220> FEATURE:
<223> OTHER INFORMATION: L-CDR1 of fusion protein

<400> SEQUENCE: 2

Gly Ala Ser Arg Asp Val Ser Ser Tyr Leu Ala
1               5                   10

<210> SEQ ID NO 3
<211> LENGTH: 15
<212> TYPE: PRT
<213> ORGANISM: Artificial Sequence
<220> FEATURE:
<223> OTHER INFORMATION: H-CDR2 of fusion protein

<400> SEQUENCE: 3

Ala Ile Ser Tyr Gly Gly Ser Ser Thr Tyr Tyr Ala Asp Ser Val
1               5                   10                  15

<210> SEQ ID NO 4
<211> LENGTH: 7
<212> TYPE: PRT
<213> ORGANISM: Artificial Sequence
<220> FEATURE:
<223> OTHER INFORMATION: L-CDR2 of fusion protein

<400> SEQUENCE: 4

Asp Ala Asn Ile Leu Gln Ser
1               5
```

```
<210> SEQ ID NO 5
<211> LENGTH: 14
<212> TYPE: PRT
<213> ORGANISM: Artificial Sequence
<220> FEATURE:
<223> OTHER INFORMATION: H-CDR3 of fusion protein

<400> SEQUENCE: 5

His Pro Ser Tyr Gly Thr Val Asn His Ala Tyr Phe Asp Val
1               5                   10

<210> SEQ ID NO 6
<211> LENGTH: 9
<212> TYPE: PRT
<213> ORGANISM: Artificial Sequence
<220> FEATURE:
<223> OTHER INFORMATION: L-CDR3 of fusion protein

<400> SEQUENCE: 6

Leu Glu Tyr Asn Asn Leu Pro Leu Thr
1               5

<210> SEQ ID NO 7
<211> LENGTH: 14
<212> TYPE: PRT
<213> ORGANISM: Artificial Sequence
<220> FEATURE:
<223> OTHER INFORMATION: H-CDR3 of fusion protein

<400> SEQUENCE: 7

His Pro Arg Tyr Gly Thr Val Asn His Ala Tyr Phe Asp Val
1               5                   10

<210> SEQ ID NO 8
<211> LENGTH: 9
<212> TYPE: PRT
<213> ORGANISM: Artificial Sequence
<220> FEATURE:
<223> OTHER INFORMATION: L-CDR3 of fusion protein

<400> SEQUENCE: 8

Leu Glu Tyr Pro Asn Leu Pro Leu Thr
1               5

<210> SEQ ID NO 9
<211> LENGTH: 14
<212> TYPE: PRT
<213> ORGANISM: Artificial Sequence
<220> FEATURE:
<223> OTHER INFORMATION: H-CDR3 of fusion protein

<400> SEQUENCE: 9

His Pro Thr Tyr Gly Thr Val Asn His Ala Tyr Phe Asp Val
1               5                   10

<210> SEQ ID NO 10
<211> LENGTH: 9
<212> TYPE: PRT
<213> ORGANISM: Artificial Sequence
<220> FEATURE:
<223> OTHER INFORMATION: L-CDR3 of fusion protein

<400> SEQUENCE: 10

Leu Glu Tyr Asn Val Leu Pro Leu Thr
1               5
```

```
<210> SEQ ID NO 11
<211> LENGTH: 9
<212> TYPE: PRT
<213> ORGANISM: Artificial Sequence
<220> FEATURE:
<223> OTHER INFORMATION: L-CDR3 of fusion protein

<400> SEQUENCE: 11

Leu Glu Tyr Asn Ser Leu Pro Leu Thr
1               5

<210> SEQ ID NO 12
<211> LENGTH: 452
<212> TYPE: PRT
<213> ORGANISM: Artificial Sequence
<220> FEATURE:
<223> OTHER INFORMATION: Heavy Chain of fusion protein

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Ala Ile Ser Tyr Gly Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Pro Ser Tyr Gly Thr Val Asn His Ala Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300
```

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
        420                 425                 430

Val Met His Glu Ala Leu His Asn His Tyr Thr Gln Lys Ser Leu Ser
    435                 440                 445

Leu Ser Pro Gly
    450

<210> SEQ ID NO 13
<211> LENGTH: 214
<212> TYPE: PRT
<213> ORGANISM: Artificial Sequence
<220> FEATURE:
<223> OTHER INFORMATION: Light Chain of fusion protein

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Gly Ala Ser Arg Asp Val Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Asn Ile Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Glu Tyr Asn Asn Leu Pro Leu
            85                  90                  95

Thr Phe Gly Gln Gly Thr Lys Val Glu Ile Lys Arg Thr Val Ala Ala
        100                 105                 110

Pro Ser Val Phe Ile Phe Pro Pro Ser Asp Glu Gln Leu Lys Ser Gly
    115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
    210

<210> SEQ ID NO 14
<211> LENGTH: 452
<212> TYPE: PRT
<213> ORGANISM: Artificial Sequence
<220> FEATURE:
<223> OTHER INFORMATION: Heavy Chain of fusion protein

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Ala Ile Ser Tyr Gly Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Pro Arg Tyr Gly Thr Val Asn His Ala Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

```
Arg Val Tyr Thr Leu Pro Pro Cys Arg Asp Glu Leu Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Val Ser Asp Gly Ser Phe Thr Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450

<210> SEQ ID NO 15
<211> LENGTH: 214
<212> TYPE: PRT
<213> ORGANISM: Artificial Sequence
<220> FEATURE:
<223> OTHER INFORMATION: Light Chain of fusion protein

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Gly Ala Ser Arg Asp Val Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Asn Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Glu Tyr Pro Asn Leu Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 16
<211> LENGTH: 452
<212> TYPE: PRT
<213> ORGANISM: Artificial Sequence
<220> FEATURE:
```

<223> OTHER INFORMATION: Heavy Chain of fusion protein

<400> SEQUENCE: 16

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Tyr Met Ser Trp Val Arg Gln Ala Pro Gly Lys Gly Leu Glu Trp Val
        35                  40                  45
Ser Ala Ile Ser Tyr Gly Gly Ser Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg His Pro Ser Tyr Gly Thr Val Asn His Ala Tyr Phe Asp Val
            100                 105                 110
Trp Gly Gln Gly Thr Leu Val Thr Val Ser Ser Ala Ser Thr Lys Gly
        115                 120                 125
Pro Ser Val Phe Pro Leu Ala Pro Ser Ser Lys Ser Thr Ser Gly Gly
    130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
        195                 200                 205
Asn His Lys Pro Ser Asn Thr Lys Val Asp Lys Lys Val Glu Pro Lys
    210                 215                 220
Ser Cys Asp Lys Thr His Thr Cys Pro Pro Cys Pro Ala Pro Glu Ala
225                 230                 235                 240
Ala Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
    290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Arg Val Tyr Thr Leu Pro Pro Cys Arg Asp Glu Leu Thr Lys Asn Gln
        355                 360                 365
Val Ser Leu Thr Cys Leu Val Lys Gly Phe Tyr Pro Ser Asp Ile Ala
    370                 375                 380
Val Glu Trp Glu Ser Asn Gly Gln Pro Glu Asn Asn Tyr Lys Thr Thr
385                 390                 395                 400
```

-continued

```
Pro Pro Val Leu Val Ser Asp Gly Ser Phe Thr Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450

<210> SEQ ID NO 17
<211> LENGTH: 452
<212> TYPE: PRT
<213> ORGANISM: Artificial Sequence
<220> FEATURE:
<223> OTHER INFORMATION: Heavy Chain of fusion protein

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Ala Ile Ser Tyr Gly Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Pro Thr Tyr Gly Thr Val Asn His Ala Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300
```

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Arg Val Tyr Thr Leu Pro Pro Cys Arg Asp Glu Leu Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Val Ser Asp Gly Ser Phe Thr Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly
    450

<210> SEQ ID NO 18
<211> LENGTH: 214
<212> TYPE: PRT
<213> ORGANISM: Artificial Sequence
<220> FEATURE:
<223> OTHER INFORMATION: Light Chain of fusion protein

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Gly Ala Ser Arg Asp Val Ser Ser Tyr
            20                  25                  30

Leu Ala Trp Tyr Gln Gln Lys Pro Gly Lys Ala Pro Lys Leu Leu Ile
            35                  40                  45

Tyr Asp Ala Asn Ile Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Glu Tyr Asn Val Leu Pro Leu
            85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

-continued

```
Phe Asn Arg Gly Glu Cys
    210

<210> SEQ ID NO 19
<211> LENGTH: 214
<212> TYPE: PRT
<213> ORGANISM: Artificial Sequence
<220> FEATURE:
<223> OTHER INFORMATION: Light Chain of fusion protein

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Gly Ala Ser Arg Asp Val Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Asn Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Glu Tyr Asn Ser Leu Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 20
<211> LENGTH: 776
<212> TYPE: PRT
<213> ORGANISM: Artificial Sequence
<220> FEATURE:
<223> OTHER INFORMATION: IDS-Fc region of fusion protein

<400> SEQUENCE: 20

Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
            20                  25                  30

Leu Val Arg Ser Pro Asn Ile Asp Gln Leu Ala Ser His Ser Leu Leu
        35                  40                  45

Phe Gln Asn Ala Phe Ala Gln Gln Ala Val Cys Ala Pro Ser Arg Val
    50                  55                  60

Ser Phe Leu Thr Gly Arg Arg Pro Asp Thr Thr Arg Leu Tyr Asp Phe
65                  70                  75                  80
```

-continued

```
Asn Ser Tyr Trp Arg Val His Ala Gly Asn Phe Ser Thr Ile Pro Gln
                85                  90                  95

Tyr Phe Lys Glu Asn Gly Tyr Val Thr Met Ser Val Gly Lys Val Phe
            100                 105                 110

His Pro Gly Ile Ser Ser Asn His Thr Asp Asp Ser Pro Tyr Ser Trp
        115                 120                 125

Ser Phe Pro Pro Tyr His Pro Ser Ser Glu Lys Tyr Glu Asn Thr Lys
130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
            180                 185                 190

Pro Phe Phe Leu Ala Val Gly Tyr His Lys Pro His Ile Pro Phe Arg
        195                 200                 205

Tyr Pro Lys Glu Phe Gln Lys Leu Tyr Pro Leu Glu Asn Ile Thr Leu
    210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
                245                 250                 255

Ser Val Pro Tyr Gly Pro Ile Pro Val Asp Phe Gln Arg Lys Ile Arg
            260                 265                 270

Gln Ser Tyr Phe Ala Ser Val Ser Tyr Leu Asp Thr Gln Val Gly Arg
        275                 280                 285

Leu Leu Ser Ala Leu Asp Asp Leu Gln Leu Ala Asn Ser Thr Ile Ile
    290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
                325                 330                 335

Tyr Val Pro Gly Arg Thr Ala Ser Leu Pro Glu Ala Gly Glu Lys Leu
            340                 345                 350

Phe Pro Tyr Leu Asp Pro Phe Asp Ser Ala Ser Gln Leu Met Glu Pro
        355                 360                 365

Gly Arg Gln Ser Met Asp Leu Val Glu Leu Val Ser Leu Phe Pro Thr
    370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
                405                 410                 415

Phe Arg Phe Arg Asp Leu Glu Glu Asp Pro Tyr Leu Pro Gly Asn Pro
            420                 425                 430

Arg Glu Leu Ile Ala Tyr Ser Gln Tyr Pro Arg Pro Ser Asp Ile Pro
        435                 440                 445

Gln Trp Asn Ser Asp Lys Pro Ser Leu Lys Asp Ile Lys Ile Met Gly
    450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
                485                 490                 495
```

-continued

```
Leu Tyr Phe Val Asp Ser Asp Pro Leu Gln Asp His Asn Met Tyr Asn
            500                 505                 510

Asp Ser Gln Gly Gly Asp Leu Phe Gln Leu Leu Met Pro Gly Gly Gly
            515                 520                 525

Gly Ser Gly Gly Gly Ser Gly Gly Ser Gly Gly Gly Ser Gly
        530                 535                 540

Gly Gly Gly Ser Gly Gly Gly Ser His Thr Cys Pro Cys Pro
545                 550                 555                 560

Ala Pro Glu Ala Ala Gly Gly Pro Ser Val Phe Leu Phe Pro Pro Lys
            565                 570                 575

Pro Lys Asp Thr Leu Met Ile Ser Arg Thr Pro Glu Val Thr Cys Val
            580                 585                 590

Val Val Asp Val Ser His Glu Asp Pro Glu Val Lys Phe Asn Trp Tyr
            595                 600                 605

Val Asp Gly Val Glu Val His Asn Ala Lys Thr Lys Pro Arg Glu Glu
            610                 615                 620

Gln Tyr Asn Ser Thr Tyr Arg Val Val Ser Val Leu Thr Val Leu His
625                 630                 635                 640

Gln Asp Trp Leu Asn Gly Lys Glu Tyr Lys Cys Lys Val Ser Asn Lys
            645                 650                 655

Ala Leu Pro Ala Pro Ile Glu Lys Thr Ile Ser Lys Ala Lys Gly Gln
            660                 665                 670

Pro Arg Glu Pro Gln Val Cys Thr Leu Pro Pro Ser Arg Asp Glu Leu
            675                 680                 685

Thr Glu Asn Gln Val Ser Leu Thr Cys Leu Val Lys Gly Phe Tyr Pro
            690                 695                 700

Ser Asp Ile Ala Val Glu Trp Glu Ser Asn Gly Gln Pro Glu Asn Asn
705                 710                 715                 720

Tyr Lys Thr Thr Pro Pro Val Leu Asp Ser Asp Gly Ser Phe Phe Leu
            725                 730                 735

Tyr Ser Trp Leu Thr Val Asp Lys Ser Arg Trp Gln Gln Gly Asn Val
            740                 745                 750

Phe Ser Cys Ser Val Met His Glu Ala Leu His Asn His Tyr Thr Gln
            755                 760                 765

Lys Ser Leu Ser Leu Ser Pro Gly
            770                 775

<210> SEQ ID NO 21
<211> LENGTH: 525
<212> TYPE: PRT
<213> ORGANISM: Artificial Sequence
<220> FEATURE:
<223> OTHER INFORMATION: IDS

<400> SEQUENCE: 21

Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
                20                  25                  30

Leu Val Arg Ser Pro Asn Ile Asp Gln Leu Ala Ser His Ser Leu Leu
            35                  40                  45

Phe Gln Asn Ala Phe Ala Gln Gln Ala Val Cys Ala Pro Ser Arg Val
        50                  55                  60

Ser Phe Leu Thr Gly Arg Arg Pro Asp Thr Thr Arg Leu Tyr Asp Phe
65                  70                  75                  80
```

```
Asn Ser Tyr Trp Arg Val His Ala Gly Asn Phe Ser Thr Ile Pro Gln
                 85                  90                  95

Tyr Phe Lys Glu Asn Gly Tyr Val Thr Met Ser Val Gly Lys Val Phe
            100                 105                 110

His Pro Gly Ile Ser Ser Asn His Thr Asp Asp Ser Pro Tyr Ser Trp
            115                 120                 125

Ser Phe Pro Pro Tyr His Pro Ser Ser Glu Lys Tyr Glu Asn Thr Lys
130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
            180                 185                 190

Pro Phe Phe Leu Ala Val Gly Tyr His Lys Pro His Ile Pro Phe Arg
            195                 200                 205

Tyr Pro Lys Glu Phe Gln Lys Leu Tyr Pro Leu Glu Asn Ile Thr Leu
        210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
                245                 250                 255

Ser Val Pro Tyr Gly Pro Ile Pro Val Asp Phe Gln Arg Lys Ile Arg
            260                 265                 270

Gln Ser Tyr Phe Ala Ser Val Ser Tyr Leu Asp Thr Gln Val Gly Arg
            275                 280                 285

Leu Leu Ser Ala Leu Asp Asp Leu Gln Leu Ala Asn Ser Thr Ile Ile
        290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
                325                 330                 335

Tyr Val Pro Gly Arg Thr Ala Ser Leu Pro Glu Ala Gly Glu Lys Leu
            340                 345                 350

Phe Pro Tyr Leu Asp Pro Phe Asp Ser Ala Ser Gln Leu Met Glu Pro
            355                 360                 365

Gly Arg Gln Ser Met Asp Leu Val Glu Leu Val Ser Leu Phe Pro Thr
        370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
                405                 410                 415

Phe Arg Phe Arg Asp Leu Glu Glu Asp Pro Tyr Leu Pro Gly Asn Pro
            420                 425                 430

Arg Glu Leu Ile Ala Tyr Ser Gln Tyr Pro Arg Pro Ser Asp Ile Pro
            435                 440                 445

Gln Trp Asn Ser Asp Lys Pro Ser Leu Lys Asp Ile Lys Ile Met Gly
        450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
                485                 490                 495

Leu Tyr Phe Val Asp Ser Asp Pro Leu Gln Asp His Asn Met Tyr Asn
```

```
                500             505             510
Asp Ser Gln Gly Gly Asp Leu Phe Gln Leu Leu Met Pro
        515             520             525

<210> SEQ ID NO 22
<211> LENGTH: 28
<212> TYPE: PRT
<213> ORGANISM: Artificial Sequence
<220> FEATURE:
<223> OTHER INFORMATION: linker

<400> SEQUENCE: 22

Gly Gly Gly Gly Ser Gly Gly Gly Gly Ser Gly Gly Gly Gly
1               5                   10                  15

Gly Ser Gly Gly Gly Gly Ser Gly Gly Gly Gly Ser
            20                  25

<210> SEQ ID NO 23
<211> LENGTH: 9
<212> TYPE: PRT
<213> ORGANISM: Artificial Sequence
<220> FEATURE:
<223> OTHER INFORMATION: Wild-type LCDR3

<400> SEQUENCE: 23

Leu Glu Tyr Asn Asn Leu Pro Leu Thr
1               5

<210> SEQ ID NO 24
<211> LENGTH: 14
<212> TYPE: PRT
<213> ORGANISM: Artificial Sequence
<220> FEATURE:
<223> OTHER INFORMATION: Wild-type HCDR3

<400> SEQUENCE: 24

His Pro Ser Tyr Gly Thr Val Asn His Ala Tyr Phe Asp Val
1               5                   10

<210> SEQ ID NO 25
<211> LENGTH: 9
<212> TYPE: PRT
<213> ORGANISM: Artificial Sequence
<220> FEATURE:
<223> OTHER INFORMATION: HL009 LCDR3

<400> SEQUENCE: 25

Leu Glu Tyr Pro Asn Leu Pro Leu Thr
1               5

<210> SEQ ID NO 26
<211> LENGTH: 14
<212> TYPE: PRT
<213> ORGANISM: Artificial Sequence
<220> FEATURE:
<223> OTHER INFORMATION: H031 HCDR3

<400> SEQUENCE: 26

His Pro Arg Tyr Gly Thr Val Asn His Ala Tyr Phe Asp Val
1               5                   10

<210> SEQ ID NO 27
<211> LENGTH: 9
<212> TYPE: PRT
<213> ORGANISM: Artificial Sequence
<220> FEATURE:
```

```
<223> OTHER INFORMATION: L016 LCDR3

<400> SEQUENCE: 27

Leu Glu Tyr Asn Val Leu Pro Leu Thr
1               5

<210> SEQ ID NO 28
<211> LENGTH: 9
<212> TYPE: PRT
<213> ORGANISM: Artificial Sequence
<220> FEATURE:
<223> OTHER INFORMATION: L113 LCDR3

<400> SEQUENCE: 28

Leu Glu Tyr Asn Ser Leu Pro Leu Thr
1               5

<210> SEQ ID NO 29
<211> LENGTH: 14
<212> TYPE: PRT
<213> ORGANISM: Artificial Sequence
<220> FEATURE:
<223> OTHER INFORMATION: H118 HCDR3

<400> SEQUENCE: 29

His Pro Thr Tyr Gly Thr Val Asn His Ala Tyr Phe Asp Val
1               5                   10
```